(12) United States Patent
Limem et al.

(10) Patent No.: US 11,766,321 B2
(45) Date of Patent: Sep. 26, 2023

(54) BREAST IMPLANT WRAPS TO LIMIT MOVEMENT OF BREAST IMPLANTS AND RELATED METHODS

(71) Applicant: Tepha, Inc., Lexington, MA (US)

(72) Inventors: Skander Limem, Melrose, MA (US); German Oswaldo Hohl Lopez, Stoneham, MA (US); Simon F. Williams, Cambridge, MA (US)

(73) Assignee: Tepha, Inc., Lexington, MA (US)

( * ) Notice: Subject to any disclaimer, the term of this patent is extended or adjusted under 35 U.S.C. 154(b) by 0 days.

(21) Appl. No.: 16/950,064

(22) Filed: Nov. 17, 2020

(65) Prior Publication Data

US 2021/0153997 A1  May 27, 2021

Related U.S. Application Data

(60) Provisional application No. 62/939,786, filed on Nov. 25, 2019.

(51) Int. Cl.
*A61F 2/12* (2006.01)
*A61F 2/00* (2006.01)

(52) U.S. Cl.
CPC .............. *A61F 2/0077* (2013.01); *A61F 2/12* (2013.01); *A61F 2220/0008* (2013.01);
(Continued)

(58) Field of Classification Search
CPC .. A61F 2/0077; A61F 2/12; A61F 2220/0008; A61F 2220/0033;
(Continued)

(56) References Cited

U.S. PATENT DOCUMENTS 2,701,879 A    2/1955  Bennett
3,280,818 A   10/1966  Pankey et al.
(Continued)

FOREIGN PATENT DOCUMENTS

CA    2829201 A1    9/2012
EP    1940312 B1    7/2009
(Continued)

OTHER PUBLICATIONS

U.S. Appl. No. 29/668,175, filed Oct. 29, 2018, Skander Limem, Entire Document.
(Continued)

*Primary Examiner* — Keri J Nelson
*Assistant Examiner* — Rebecca Lynee Zimmerman
(74) *Attorney, Agent, or Firm* — Wolf, Greenfield & Sacks, P.C.

(57) ABSTRACT

Described herein are breast implant fixation devices for use in breast reconstruction and breast augmentation. Novel wraps are designed to avert lateral displacement and bottoming out of breast implants, reduce capsular contraction and implant extrusion, eliminate skin indentations and ripples caused by breast implants, and reduce or eliminate palpability. The wraps are adapted to securely fold around the breast implants, limiting relative movement between the wrap and breast implant and reducing wrinkles. Tissue in-growth into the wraps limits movement of the wrap-breast implant assembly and thereby limits movement of the breast implant.

28 Claims, 6 Drawing Sheets

(52) U.S. Cl.
CPC . *A61F 2220/0033* (2013.01); *A61F 2230/005* (2013.01); *A61F 2230/0006* (2013.01); *A61F 2250/0018* (2013.01)

(58) Field of Classification Search
CPC ........ A61F 2230/0006; A61F 2230/005; A61F 2250/0018; A61F 2220/00; A61F 2250/0023; A61F 2/0063
See application file for complete search history.

(56) References Cited

U.S. PATENT DOCUMENTS

| | | |
|---|---|---|
| 3,293,663 A | 12/1966 | Cronin |
| 3,366,975 A | 2/1968 | Pangman |
| 3,934,593 A | 1/1976 | Mellinger |
| 4,372,293 A | 2/1983 | Vijil-Rosales |
| 4,380,569 A | 4/1983 | Shaw |
| 4,388,735 A | 6/1983 | Ionescu et al. |
| 4,773,909 A | 9/1988 | Chaglassian |
| 4,801,299 A | 1/1989 | Brendel et al. |
| 4,863,470 A | 9/1989 | Carter |
| 4,936,858 A | 6/1990 | O'Keeffe |
| 4,960,425 A | 10/1990 | Yan et al. |
| 5,007,929 A | 4/1991 | Quaid |
| 5,011,494 A | 4/1991 | von Recum et al. |
| 5,217,494 A | 6/1993 | Coggins et al. |
| 5,356,429 A | 10/1994 | Seare |
| 5,383,929 A | 1/1995 | Ledergerber |
| 5,480,430 A | 1/1996 | Carlisle et al. |
| 5,500,019 A | 3/1996 | Johnson et al. |
| 5,545,221 A | 8/1996 | Hang-Fu |
| 5,584,884 A | 12/1996 | Pignataro |
| 5,658,328 A | 8/1997 | Johnson |
| 5,658,329 A | 8/1997 | Purkait |
| 5,676,161 A | 10/1997 | Breiner |
| 5,716,404 A | 2/1998 | Vacanti et al. |
| 5,755,611 A | 5/1998 | Noble et al. |
| 5,759,204 A | 6/1998 | Seare |
| 5,902,335 A | 5/1999 | Snyder, Jr. |
| 5,990,378 A | 11/1999 | Ellis |
| 6,074,421 A | 6/2000 | Murphy |
| 6,113,634 A | 9/2000 | Weber-Unger et al. |
| 6,146,418 A | 11/2000 | Berman |
| 6,210,439 B1 | 4/2001 | Firmin et al. |
| 6,328,765 B1 | 12/2001 | Hardwick et al. |
| 6,368,541 B1 | 4/2002 | Pajotin et al. |
| 6,371,831 B1 | 4/2002 | Dodge |
| 6,544,287 B1 | 4/2003 | Johnson et al. |
| 6,599,323 B2 | 7/2003 | Melican et al. |
| 6,682,559 B2 | 1/2004 | Myers et al. |
| 6,723,133 B1 | 4/2004 | Pajotin |
| 6,740,122 B1 | 5/2004 | Pajotin |
| 6,913,626 B2 | 7/2005 | Mcghan |
| 7,081,135 B2 | 7/2006 | Smith et al. |
| D539,506 S | 4/2007 | Valentin |
| 7,476,249 B2 | 1/2009 | Frank |
| 7,520,896 B2 | 4/2009 | Benslimane |
| 7,670,372 B2 | 3/2010 | Shfaram et al. |
| 7,875,074 B2 | 1/2011 | Chen et al. |
| 7,998,202 B2 | 8/2011 | Lesh |
| 8,007,531 B2 | 8/2011 | Frank |
| 8,034,270 B2 | 10/2011 | Martin et al. |
| 8,043,373 B2 | 10/2011 | Schuessler et al. |
| 8,101,116 B2 | 1/2012 | Lindh, Sr. et al. |
| 8,211,173 B2 | 7/2012 | Keller et al. |
| 8,377,127 B2 | 2/2013 | Schuessler |
| 8,506,582 B2 | 8/2013 | Kammerer et al. |
| 8,728,159 B2 | 5/2014 | Kim et al. |
| 8,778,020 B2 | 7/2014 | Gregg et al. |
| 8,858,629 B2 | 10/2014 | Moses et al. |
| 8,911,765 B2 | 12/2014 | Moses et al. |
| 8,936,504 B2 | 1/2015 | Deal et al. |
| 8,986,377 B2 | 3/2015 | Richter et al. |
| 9,277,986 B2 | 3/2016 | Moses et al. |
| 9,474,598 B2 | 10/2016 | Gregg et al. |
| 9,532,867 B2 | 1/2017 | Felix et al. |
| 9,555,155 B2 | 1/2017 | Ganatra et al. |
| 9,585,744 B2 | 3/2017 | Moses et al. |
| 9,603,698 B2 | 3/2017 | Kerr et al. |
| 9,636,211 B2 | 5/2017 | Felix et al. |
| 9,655,715 B2 | 5/2017 | Limem et al. |
| 9,700,411 B2 | 7/2017 | Klima et al. |
| 9,707,073 B2 | 7/2017 | Al-Jasim |
| 9,713,350 B1 | 7/2017 | Colburn |
| 9,713,524 B2 | 7/2017 | Glicksman |
| D799,152 S | 10/2017 | Brownell et al. |
| D803,401 S | 11/2017 | Limem et al. |
| D816,220 S | 4/2018 | Limem et al. |
| D816,221 S | 4/2018 | Limem et al. |
| 10,028,818 B2 | 7/2018 | Felix et al. |
| 10,052,192 B2 | 8/2018 | Schuessler et al. |
| 10,058,417 B2 | 8/2018 | Limem et al. |
| D836,778 S | 12/2018 | Limem et al. |
| 10,258,460 B2 | 4/2019 | Moses et al. |
| 10,363,127 B2 | 7/2019 | Mlodinow et al. |
| D856,517 S | 8/2019 | Spiegel et al. |
| D857,895 S | 8/2019 | Limem et al. |
| 10,405,969 B2 | 9/2019 | Bertoli et al. |
| 16,587,903 | 9/2019 | Limem |
| 10,449,034 B2 | 10/2019 | Bowley et al. |
| 62,939,786 | 11/2019 | Limem |
| D870,289 S | 12/2019 | Limem et al. |
| 10,568,728 B2 | 2/2020 | Felix et al. |
| 10,595,986 B2 | 3/2020 | Rehnke |
| D888,244 S | 6/2020 | Limem et al. |
| 10,695,165 B2 | 6/2020 | Shetty et al. |
| D889,654 S | 7/2020 | Limem et al. |
| D889,655 S | 7/2020 | Limem et al. |
| 10,722,345 B2 | 7/2020 | Limem et al. |
| D892,329 S | 8/2020 | Limem et al. |
| D894,393 S | 8/2020 | Limem et al. |
| D896,383 S | 9/2020 | Schuessler et al. |
| 10,765,507 B2 | 9/2020 | Moses et al. |
| D926,984 S | 8/2021 | Schuessler et al. |
| D927,690 S | 8/2021 | Limem et al. |
| 11,154,393 B2 | 10/2021 | Limem et al. |
| D956,977 S | 7/2022 | Limem et al. |
| 2002/0022883 A1 | 2/2002 | Burg |
| 2002/0143396 A1 | 10/2002 | Falcon et al. |
| 2002/0165596 A1 | 11/2002 | Wilson |
| 2003/0195620 A1 | 10/2003 | Huynh et al. |
| 2003/0207649 A1 | 11/2003 | Reeder |
| 2003/0212461 A1 | 11/2003 | Vadurro et al. |
| 2003/0212462 A1 | 11/2003 | Gryska et al. |
| 2004/0225352 A1 | 11/2004 | Osborne et al. |
| 2005/0027348 A1 | 2/2005 | Case et al. |
| 2006/0167338 A1 | 7/2006 | Shfaram et al. |
| 2006/0211334 A1 | 9/2006 | Smith |
| 2007/0055371 A1 | 3/2007 | Laghi |
| 2007/0088434 A1 | 4/2007 | Frank |
| 2007/0135929 A1 | 6/2007 | Williams et al. |
| 2007/0196421 A1 | 8/2007 | Hunter et al. |
| 2007/0198085 A1 | 8/2007 | Benslimane |
| 2008/0027273 A1 | 1/2008 | Gutterman |
| 2008/0082113 A1 | 4/2008 | Bishop et al. |
| 2008/0097601 A1 | 4/2008 | Codori-Hurff et al. |
| 2008/0128315 A1 | 6/2008 | Buevich et al. |
| 2008/0154366 A1 | 6/2008 | Frank |
| 2008/0241212 A1 | 10/2008 | Moses et al. |
| 2009/0082864 A1 | 3/2009 | Chen et al. |
| 2009/0240342 A1 | 9/2009 | Lindh, Sr. et al. |
| 2009/0248071 A1 | 10/2009 | Saint et al. |
| 2010/0021738 A1 | 1/2010 | Maida et al. |
| 2010/0023120 A1 | 1/2010 | Holecek et al. |
| 2010/0030015 A1 | 2/2010 | Delorme et al. |
| 2010/0042211 A1 | 2/2010 | Epps et al. |
| 2010/0137679 A1 | 6/2010 | Lashinski et al. |
| 2010/0191330 A1 | 7/2010 | Lauryssen et al. |
| 2010/0204791 A1 | 8/2010 | Shfaram et al. |
| 2010/0217388 A1 | 8/2010 | Cohen et al. |
| 2010/0249924 A1 | 9/2010 | Powell et al. |
| 2010/0249947 A1 | 9/2010 | Lesh et al. |
| 2010/0305696 A1 | 12/2010 | Mao et al. |
| 2010/0331612 A1 | 12/2010 | Lashinski et al. |

(56) References Cited

U.S. PATENT DOCUMENTS

| | | |
|---|---|---|
| 2011/0009960 A1 | 1/2011 | Altman et al. |
| 2011/0022171 A1 | 1/2011 | Richter et al. |
| 2011/0257665 A1 | 10/2011 | Mortarino |
| 2011/0264213 A1 | 10/2011 | DeMiranda |
| 2011/0276122 A1 | 11/2011 | Schlick et al. |
| 2011/0301706 A1 | 12/2011 | Brooks et al. |
| 2012/0004723 A1 | 1/2012 | Mortarino et al. |
| 2012/0021738 A1 | 1/2012 | Koo et al. |
| 2012/0022646 A1 | 1/2012 | Mortarino et al. |
| 2012/0158134 A1 | 6/2012 | Codori-Hurff et al. |
| 2012/0185041 A1 | 7/2012 | Mortarino et al. |
| 2012/0221105 A1 | 8/2012 | Altman et al. |
| 2012/0226352 A1 | 9/2012 | Becker |
| 2012/0232653 A1 | 9/2012 | Saint et al. |
| 2012/0266348 A1 | 10/2012 | Meginnis |
| 2012/0283826 A1 | 11/2012 | Moses et al. |
| 2013/0066423 A1 | 3/2013 | Bishop et al. |
| 2013/0103149 A1 | 4/2013 | Altman et al. |
| 2013/0116778 A1 | 5/2013 | Gregg et al. |
| 2013/0178699 A1 | 7/2013 | Saint et al. |
| 2013/0178875 A1 | 7/2013 | Horton et al. |
| 2013/0253645 A1 | 9/2013 | Kerr et al. |
| 2013/0304098 A1 | 11/2013 | Mortarino |
| 2014/0017284 A1 | 1/2014 | Yang et al. |
| 2014/0046442 A1 | 2/2014 | Guterman |
| 2014/0081398 A1 | 3/2014 | Mejia et al. |
| 2014/0135925 A1 | 5/2014 | Brooks et al. |
| 2014/0163696 A1 | 6/2014 | Lesh et al. |
| 2014/0200396 A1 | 7/2014 | Lashinski et al. |
| 2014/0222146 A1 | 8/2014 | Moses et al. |
| 2014/0222161 A1 | 8/2014 | Mathisen |
| 2014/0257482 A1 | 9/2014 | Ward et al. |
| 2014/0276993 A1 | 9/2014 | Reilly et al. |
| 2014/0276997 A1 | 9/2014 | Harrah et al. |
| 2015/0012089 A1 | 1/2015 | Shetty et al. |
| 2015/0018946 A1 | 1/2015 | Guterman |
| 2015/0056131 A1 | 2/2015 | Bernasconi et al. |
| 2015/0081000 A1 | 3/2015 | Hossainy et al. |
| 2015/0112434 A1 | 4/2015 | Felix et al. |
| 2015/0134043 A1 | 5/2015 | Irwin et al. |
| 2015/0223928 A1 | 8/2015 | Limem et al. |
| 2015/0272722 A1 | 10/2015 | Davila et al. |
| 2015/0351889 A1 | 12/2015 | Reddy et al. |
| 2015/0351891 A1 | 12/2015 | Moses et al. |
| 2015/0351899 A1 | 12/2015 | Mortarino |
| 2015/0351900 A1 | 12/2015 | Glicksman |
| 2016/0022416 A1 | 1/2016 | Felix et al. |
| 2016/0038269 A1 | 2/2016 | Altman et al. |
| 2016/0106538 A1 | 4/2016 | Mitra et al. |
| 2016/0151062 A1* | 6/2016 | Bachrach ......... A61B 17/12009 606/221 |
| 2016/0151138 A1 | 6/2016 | Guterman et al. |
| 2016/0166727 A1 | 6/2016 | Ganatra et al. |
| 2016/0256268 A1 | 9/2016 | Dakin |
| 2016/0296329 A1 | 10/2016 | Alkhatib et al. |
| 2016/0310262 A1 | 10/2016 | Doucet et al. |
| 2017/0014226 A1 | 1/2017 | Fenaroli |
| 2017/0065403 A1 | 3/2017 | Al-Jasim |
| 2017/0143475 A1 | 5/2017 | Moses et al. |
| 2017/0196672 A1 | 7/2017 | Guterman |
| 2017/0216009 A1 | 8/2017 | Felix et al. |
| 2017/0216018 A1 | 8/2017 | Limem et al. |
| 2017/0224471 A1 | 8/2017 | Rehnke |
| 2018/0055624 A1 | 3/2018 | Barere et al. |
| 2018/0303599 A1 | 10/2018 | Al-Jasim |
| 2018/0325644 A1 | 11/2018 | Felix et al. |
| 2019/0216595 A1 | 7/2019 | Moses et al. |
| 2019/0247180 A1 | 8/2019 | Limem et al. |
| 2019/0254807 A1 | 8/2019 | Limem et al. |
| 2020/0085526 A1 | 3/2020 | Schuessler et al. |
| 2020/0100892 A1 | 4/2020 | Limem et al. |
| 2020/0261202 A1 | 8/2020 | Mathisen et al. |
| 2020/0276006 A1 | 9/2020 | Felix et al. |
| 2020/0360129 A1 | 11/2020 | Moses et al. |
| 2020/0397554 A1 | 12/2020 | Epps et al. |
| 2020/0405473 A1* | 12/2020 | Nanni ................... A61L 27/362 |
| 2021/0069374 A1 | 3/2021 | Brennan et al. |
| 2021/0251738 A1* | 8/2021 | Young .................... A61L 27/54 |
| 2022/0079741 A1 | 3/2022 | Limem et al. |
| 2022/0079742 A1 | 3/2022 | Limem et al. |
| 2022/0362001 A1 | 11/2022 | Felix et al. |

FOREIGN PATENT DOCUMENTS

| | | |
|---|---|---|
| EP | 2903563 A1 | 8/2015 |
| EP | 2903563 B1 | 11/2017 |
| EP | 2190382 B1 | 10/2018 |
| JP | 2004-130118 A | 4/2004 |
| JP | 4296399 B2 | 7/2009 |
| WO | 2004096098 A1 | 11/2004 |
| WO | 2006117622 A1 | 11/2006 |
| WO | 2007004214 A3 | 5/2007 |
| WO | 2009001293 A1 | 12/2008 |
| WO | 2009050706 A2 | 4/2009 |
| WO | 2011119742 A2 | 9/2011 |
| WO | 2012012215 A2 | 1/2012 |
| WO | 2012122215 A2 | 9/2012 |
| WO | WO 2014/041577 A1 | 3/2014 |
| WO | 2015006737 A1 | 1/2015 |
| WO | 2019094861 A1 | 5/2019 |
| WO | 2019119060 A1 | 6/2019 |
| WO | 2019175911 A2 | 9/2019 |
| WO | WO 2019/243599 A1 | 12/2019 |
| WO | 2020070694 A1 | 4/2020 |
| WO | WO 2020/072349 A1 | 4/2020 |
| WO | 2020242694 A1 | 12/2020 |
| WO | 2021015976 A1 | 1/2021 |
| WO | 2021024284 A1 | 2/2021 |
| WO | WO 2021/063850 A1 | 4/2021 |
| WO | WO-2021063851 A * | 4/2021 |

OTHER PUBLICATIONS

"GalaFLEX Mesh . . . Supporting Your Quest for Timeless Beauty," Tepha, Inc. 400109 Rev.B, Oct. 2012.

"GalaFLEX Mesh," Tepha Inc., www.galateasurgical.com, P/N 400124, Rev.A, Oct. 2013.

Auclair, et al, "Repair of mammary ptosis by insertion of an internal absorbable support and periareaolar scar," Ann Chir Plast Esthet, 1993, 38, No. 1, pp. 107-113.

Bertozzi, N. Ann Med Surg. 21 :34-44 (2017).

Damino, et al., "Comparison of the capsular response to the Biocell RIV and Mentor 1600 Siltex breast implant surface texturing: a scanning electron microscopic study", Plast. Reconstr. Surg. 2001, 108(7), 2047-2052.

DeBruijn, et al, "Mastopexy with Mesh Reinforcement: The Mechanical Characteristics of Polyester Mesh in the Female Breast," Plast. Reconstr. Surg. 124: 364, 2009.

DeBruijn,et al, "Mastopexy with 3D Preshaped Mesh for Long Term Results: Development of the Internal Bra System," Aesth Plast Surg., 32:757-765, DOI 10.1007/s00266-008-9186-y, 2008.

European Search and Opinion dated Jul. 3, 2017, for 12754773.5-1666.

Goes, "Periareolar mammaplasty: double skin technique with application of polyglactine or mixed mesh," Plast. Reconstr. Surg.97-959-68 (1996).

Goes, "Periareolar mammaplasty: double-skin technique with application of mesh support," Clin Plastic Surg 29 (2002) 349-364.

Goes, "Periareolar Mastopexy with FortaPerm," Aesth. Plast. Surg., 34-350-8, 2010.

Gorbet et al. Biomaterials, 26:6811-6817 (2005).

ISR and Written Opinion for PCT/US2019/015849, dated Apr. 23, 2019.

Johnson, Gerald W., "Central core reduction mammoplasties and Marlex suspension of breast tissue," Aesthetic Plastic Surgery 5:77-84, 1981.

Leberfinger et al., "Breast-implant associated anaplastic large cell lymphoma: a systematic review", JAMA Surg. Dec. 1, 2017; 152(12), 1161-1168.

(56) References Cited

OTHER PUBLICATIONS

Malluci, Concepts in aesthetic breast dimensions: Analysis of the ideal breast, Journal of Plastic, Reconstructive & Aesthetic Surgery (2012) 65, p. 8-16.
Malluci, Design for Natural Breast Augmentation: The ICE Principle, Plastic and Reconstructive Surgery, Jun. 2016, vol. 137. No. 6, 1728-1737.
Malluci, Population Analysis of the Perfect Breast: A Morphometric Analysis, (2014), www.PRSJournal.com, vol. 134, No. 3 • The Perfect Breast, p. 436- 447.
Maxwell and Gabriel, "The evolution of breast implants", Plast. Reconstr. Surg. 134:12S, 2014.
O'Shaughnessy, "Evolution and update on current devices for prosthetic breast reconstruction", Gland Surgery, 2015, 4(2):97-110.
P. van Deventer, Improving the Longevity and Results of Mastopexy and Breast Reduction Procedures: Reconstructing an Internal Breast Support System with Biocompatible Mesh to Replace the Supporting Function of the Ligamentous Suspension, Aesth Plast Surg (2012) 36:578-589, DOI 10.1007/s00266-011-9845-2.
Ray, J.A. et al., "Polydioxanone (PDS), A Novel Monofilament Synthetic Absorbable Suture", Surgery, Gynecology & Obstetrics, Oct. 1981, vol. 153, 497-507.
Sieber et al., "Clinical evaluation of shaped gel breast implant rotation using high-resolution ultrasound", Aesthetic Surgery Journal, 2017, vol. 37 (3), 290-296.
Slavin, "The use of acellular dermal matrices in revisional breast reconstruction", Plast. Reconstr. Surg. 2012, 130(Suppl. 2): 70S-85S.
Supplementary European Search Report of the EPO dated Jul. 30, 2014, EP 12754773.5 from PCT/US2012/027075.
Williams "Poly-4-hydroxputyrate (P4HB): a new generation of resorbable medical devices for tissue repair and regeneration," DOI 10.1515/bmt-2013-0009 Biomed Tech 2013; 58(5): 439-452.
Written Opinion of IPEA dated Jun. 15, 2015 for PCT/US2014/046420.
Written Opinion of ISR dated Nov. 5, 2012 for PCT/US2012/027975.
Written Opinion of the ISA, dated Apr. 13, 2021, for PCT/US2020/060809.
U.S. Appl. No. 17/871,155, filed Jul. 22, 2022, Felix et al.
EP 19869949.8, dated May 31, 2022, Extended European Search Report.
Extended European Search Report for European Application 19869949.8 dated May 31, 2022.
U.S. Appl. No. 16/587,903, filed Sep. 30, 2019, Limem et al.
U.S. Appl. No. 16/797,960, filed Feb. 21, 2020, Felix et al.
U.S. Appl. No. 17/486,879, filed Sep. 27, 2021, Limem et al.
U.S. Appl. No. 17/486,886, filed Sep. 27, 2021, Limem et al.
U.S. Appl. No. 29/735,730, filed May 22, 2020, Limem et al.
U.S. Appl. No. 29/736,445, filed May 9, 2020, Limem et al.
U.S. Appl. No. 29/798,823, filed Jul. 10, 2021, Limem et al.

\* cited by examiner

BREAST IMPLANT WRAPS TO LIMIT MOVEMENT OF BREAST IMPLANTS AND RELATED METHODS

CROSS-REFERENCE TO RELATED APPLICATIONS

This Application claims the benefit under 35 U.S.C. § 119(e) of U.S. Provisional Application Serial No. 62/939,786, filed Nov. 25, 2019, the entire contents of which is incorporated herein by reference in its entirety.

FIELD OF THE INVENTION

The present invention generally relates to the field of surgery, and more particularly, to implantable medical devices that limit the movement of breast implants following breast reconstruction, including augmentation mastopexy.

BACKGROUND OF THE INVENTION

Breast reconstruction following mastectomy has become an integral and important part of breast cancer treatment with the surgery providing the patient with both aesthetic and psychosocial benefits. Nearly 65% of US breast reconstruction procedures now use a tissue expander (TE) which is temporarily implanted in the breast to create a pocket for a permanent breast implant in the first step of the procedure. Tissue expanders are now more frequently placed on top of the chest muscle (pre-pectoral placement) rather than under the chest muscle in order to reduce postoperative pain. Once a pocket is created, the TE is removed and replaced with a permanent breast implant in a second step. In some patients, however, it is possible to form a pocket for the breast implant following mastectomy without the use of a TE.

Breast implants can also be used in breast augmentation and mastopexy procedures to augment breast size. In the latter procedure, a breast lift is combined with breast augmentation. Most commonly, the breast implant is placed in a pocket under the breast tissue, but in some cases, it is implanted under the chest wall.

Breast implants differ in dimensions, shape, and surface texture. A wide variety of different dimensions are available allowing the surgeon and patient to select from a range of projections, heights, widths and overall volume. In terms of shape, there are round and anatomically shaped implants, and the surfaces of the implants may be smooth, micro-textured or macro-textured. The Siltex 1600 micro-textured breast implant, for example, has a surface with small open-pores of 70-150 µm diameters and depths of 40-100 µm, while the Biocell RTV macro-textured breast implant has larger open pores of 600-800 µm diameter with depths of 150-200 µm (Damino et al. Comparison of the capsular response to the Biocell RTV and Mentor 1600 Siltex breast implant surface texturing: a scanning electron microscopic study, Plastic and Reconstructive Surgery, 2001, 108(7), 2047-2052).

Texturing of breast implants was initially used as a method to limit breast implant rotation and movement. However, recent studies using high-resolution ultrasound have discovered that macro-texturing is not sufficient to prevent breast implant rotation. For example, Sieber et al. (Clinical evaluation of shaped gel breast implant rotation using high-resolution ultrasound, Aesthetic Surgery Journal, 2017, Vol 37 (3), 290-296) have reported that the breast implant rotation rate in patients implanted with anatomical breast implants manufactured by Mentor and Allergan was 27%. Furthermore, a staggering 26% of the breast implants checked had rotated 45° from the midline. Sieber et al. concluded that rotation of breast implants was occurring in 42% of patients. Capsule formation around breast implants likely prevents the breast implant from being secured in place.

Obviously, no patient wants to discover that their anatomical implant has rotated, and that the thicker part of the implant is no longer located at the bottom of the breast, but instead is located to the side or even at the top of the breast. Particularly when the only way to resolve the problem is by further surgery.

Concern over the use of macro-textured anatomical breast implants is not limited to undesirable rotation of the implants resulting in a suboptimal appearance of the breasts. A growing body of evidence is associating the use of these implants with a serious rise in cases of anaplastic large cell lymphoma (ALCL), a rare peripheral T-cell lymphoma, that can be fatal (Leberfinger et al., Breast-implant associated anaplastic large cell lymphoma: a systematic review, JAMA Surg. 2017, Dec. 1; 152(12), 1161-1168). Chronic inflammation resulting from the macro-texturing of the anatomical breast implants is thought to be the underlying mechanism. The chronic inflammation is believed in certain cases to trigger a malignant transformation of T cells resulting in a cancer of the immune system. Treatment of the lymphoma involves removal of the patient's implant and the capsule surrounding the implant, and in more advanced cases, the patient may require further treatment including radiotherapy, chemotherapy, and lymph node dissection. On account of the rise in cases of breast implant-ALCL, the FDA has advised patients to discuss the risks associated with breast implants that have macro-textured surfaces, as well as smooth surfaces, and some surgeons are decreasing or discontinuing their use of macro-textured breast implants.

While rotation of smooth breast implants does not necessarily change the appearance of the breast, breast implant-ALCL with smooth breast implants has been reported albeit at a lower incidence rate than with patients implanted with macro-textured anatomical implants. Furthermore, it has been reported that the rate of capsular contraction, which results from a thickening of the thin flexible capsule that initially surrounds the implant, is higher for smooth implants than for anatomical implants (Damino, et al., Comparison of the capsular response to the Biocell RTV and Mentor 1600 Siltex breast implant surface texturing: a scanning electron microscopic study, Plast. Reconstr. Surg. 2001, 108(7), 2047-2052). While the reason for the greater rate of capsule contraction is not fully understood, it has been postulated that the higher rate of capsule contraction results from a higher rate of rotation and more movement of the smooth round breast implants. Capsular contraction can be a serious problem, and is relatively common. It can occur soon after implantation or 20-30 years later. Contraction of the capsule that forms around the implant can cause chronic pain, and a feeling of tightness around the breast. This can be treated either by capsulotomy where the implant is removed, incisions are made in the capsule, and the implant is replaced. Or, contraction of the capsule can be treated by capsulectomy where both the implant and the capsule are removed, and a new implant is implanted in the patient. Avoiding the need to perform these procedures would be preferable.

In addition to the problems associated with the rotation of breast implants, movement of either type of breast implant is undesirable because it will produce an unnatural appearance of the breast. Despite movement of breast implants being undesirable, it is still not unusual. In one study of 715 reconstruction patients, 71.5% of patients at 10 years had undergone reoperation for implant malposition (O'Shaughnessy, 2015, Evolution and update on current devices for prosthetic breast reconstruction, Gland Surgery, 4(2):97-110). Displacements of a breast implant can occur if the shape of the pocket for the implant is not precise, and physical activity can also result in implant displacement. Movement of an implant can also occur if supporting tissues around the implant stretch or become thinner, or if there is a loss of elasticity of the tissues. These conditions can, for example, result in "bottoming out" where the implant moves lower resulting in an unattractive appearance (see, Slavin, 2012, The use of acellular dermal matrices in revisional breast reconstruction, Plast. Reconstr. Surg. 130 (Suppl. 2): 70S-85S). These conditions can also result in the implant pocket stretching laterally causing the patient's breast implants to move sideways towards their sides or arm pits, particularly when lying down.

Various implantable devices have been developed to create pockets for breast implants or for use as slings in breast reconstruction. Acelluar dermal matrix (ADM), for example, has been used to cover tissue expanders (Bertozzi, N. Ann Med Surg. 21:34-44 (2017)). In a typical procedure, the pectoralis major muscle is mobilized, and the ADM is attached to the edge of the muscle in order to create a sling and submuscular pocket for the tissue expander. The use of ADM eliminates the need to release and elevate the serratus anterior muscle, the pectoralis minor muscle, and the rectus abdominis fascia, and consequently reduces postoperative pain. Such devices, however, are not designed to limit rotation of breast implants.

U.S. Pat. No. 4,936,858 to O'Keeffe also discloses pouches for breast implants, made from non-biodegradable yarn. The diameters of the pouches exceed that of the implant by approximately 20%. The pouches are not designed to limit rotation of the breast implants.

U.S. Pat. No. 7,520,896 to Benslimane shows a breast implant with a support element (5) attached to the breast implant using adhesive (4), and a securing element (3) connected to the support element. The support element (5) can be attached to the patient's pectoral muscle or in the area of the axilla. FIG. 5 of Benslimane shows a breast implant that comprises two packages, an outer package and an inner package designed to prevent contamination of the breast implant by microbes. The outer package is non-sterile. The pouch, however, is not designed to limit rotation or migration of any breast implant, and is not designed for implantation since the outer package is non-sterile.

US Patent Application No. 20070196421 to Hunter discloses sleeves for breast implants that comprise fibrosis-inhibiting drugs, but does not disclose sleeves that are designed to limit rotation of breast implants.

US Patent Application No. 20080128315 to Buevich discloses resorbable pouches for implantable medical devices, but does not disclose pouches for breast implants, or pouches designed to limit rotation of breast implants.

US Patent Application No. 20020165596 to Wilson discloses resorbable pouches for placement of bone graft or bone graft substitutes, but does not discloses pouches for breast implants, or pouches designed to limit rotation of breast implants.

U.S. Pat. No. 5,383,929 to Ledergerber discloses coverings for implants that disorganize scar tissue at the implant/body interface. The coverings are preferably made from expanded PTFE, a non-degradable polymer.

WO2019/094861 to Mlodinow discloses mesh pouches for securing implants within a patient's body. The mesh pouches may be used to support a breast implant. Janhofer et al., The suture tab technique: Securing implant position in prepectoral breast reconstruction, Plast Reconstr Surg Glob Open, 2018; 6:e2005, discloses the use of ADM to fixate breast implants.

Notwithstanding the above, there is still a need for breast implant fixation devices as described herein that can limit the movement and rotation of breast implants, and reduce capsular contraction. In particular, there is a need to develop breast implant fixation devices that can remove the need to rely on the anatomy of the breast pocket to achieve the desired anatomical position of the breast implant. Such breast pockets can be highly variable and inconsistent, particularly after mastectomy, making it difficult to maintain the correct vertical positioning of the breast implant, and inferolateral stability. There is also a need to develop breast implant fixation devices that not only limit movement of breast implants, but prevent the breast implant from being palpable, or that hide any ripples or indentations in the breast resulting from implantation of breast implants. Such devices would provide an improved aesthetic outcome for patients. There is also another need to provide breast implant fixation devices that make it easier to position and secure breast implants, and minimize breast implant motion, migration, and the effect of gravity on breast implants.

SUMMARY OF THE INVENTION

Medical devices are described herein that limit the movement of breast implants. In embodiments, breast implants may be at least partially covered by a breast implant fixation device comprising a porous polymeric two-dimensional wrap. The wrap may be anchored in the breast, and thereby minimize movement of the breast implant. The wrap may further comprise one or more tabs to provide additional sites for fixation of the wrap in the breast. The wrap or tabs may be fixated to the pectoralis major muscle and or the patient's chest wall. The wrap or tabs may be sutured or stapled to fixate and anchor the wrap in the breast of the patient. The wraps may also prevent the breast implants from being palpable, or prevent the formation of ripples or indentations on the skin following placement of the breast implants in the breasts. The wraps limit movement of the breast implants by allowing tissue in-growth into the wraps, and by anchoring of the wraps to the chest wall. The breast implants may be fully or partially encased by the wraps. The wraps eliminate the problem of palpability or formation of skin indentations and ripples by providing a layer between the patient's skin and the breast implant.

Methods to prepare the wraps are also described. The wraps are preferably made with absorbable polymers, most preferably with poly-4-hydroxybutyrate (P4HB) and copolymers thereof, or poly(butylene succinate) or copolymers thereof. The wraps are preferably prepared with porosity that allows tissue in-growth, and anchoring of the wraps at the site of implantation. Preferably, the wraps are prepared with fibers, and most preferably with monofilament fibers or dry spun fibers. Preferred methods of manufacturing the wraps include knitting, and dry spinning.

Also disclosed are methods of using the wraps with breast implants in breast reconstruction, and breast augmentation, including augmentation mastopexy. The breast implants may be filled, for example, with silicone or saline. The wraps may be used following mastectomy, and may be used in either one-stage or two-stage breast reconstruction procedures. In the latter case, a preferred method involves mobilizing the pectoralis major muscle, creating a submuscular pocket for a tissue expander (TE), optionally by attaching an acellular dermal matrix, P4HB textile or textile comprising polybutylene succinate or copolymer thereof to the elevated pectoralis major muscle, inflating the TE, removing the TE, and implanting the wrap containing a breast implant in the submuscular pocket.

In breast augmentation procedures, the wrap containing a breast implant may be placed in a breast pocket created either in the subglandular position (above the pectoral muscle) or in the submuscular position (below the pectoral muscle), but the former is preferred. When used in breast augmentation, the wrap and breast implant may be inserted using transaxillary or transumbilical methods, or following a peri-areolar incision or incision at the inframammary fold (IMF).

A wrap for a breast implant to prevent movement of the breast implant in a patient comprises a base section, a cover section, and a hinge region connecting the base section to the cover section. Each of the base section and cover section, and optionally the hinge region, are made of a material comprising a plurality of pores for tissue ingrowth. The wrap preferably comprises one or more connectors that can be used to secure the breast implant inside the wrap.

Preferably, the wrap comprises one or more tabs to provide additional sites for fixation of the wrap in the breast. More preferably, the wrap comprises a superior tab. The superior tab can be used to fixate the wrap to the pectoralis major muscle in order to maintain the vertical positioning of the breast implant, prevent inferolateral instability, and minimize implant motion.

In embodiments, the breast implant fixation device comprises a wrap comprising a first substantially planar 2D configuration, and a second 3D configuration when the breast implant is wrapped in the wrap.

In another embodiment, the breast implant fixation device comprises a wrap comprising a cover section for placement between the breast implant and the skin of the patient, and a base section for placement on the chest wall of the patient.

In embodiments, the breast implant fixation device comprises a wrap comprising a base section, cover section, and hinge region. The base section, cover section and hinge region may form a two-dimensional unitary unit that can be formed into a three-dimensional shape to at least partially cover a breast implant.

In embodiments, the breast implant fixation device comprises a wrap comprising connectors that secure the breast implant inside the wrap. The connectors preferably connect the cover section to the base section.

In embodiments, the breast implant fixation device comprises a wrap with a cover section and a base section, and may further comprise one or more fixation tabs. The fixation tabs may be located on the cover section or base section. In embodiments, the wrap comprises a tab for fixation that is located in a superior position on the wrap when the breast implant is at least partially covered by the wrap and placed in the breast.

In an alternative embodiment, the breast implant fixation device comprises a base section and a cover section that are separate from one another. The device may be assembled to wrap the breast implant by placing the breast implant on the base section of the device, placing the cover section on the front of the breast implant, and securing the base section and cover section together around the breast implant. More preferably, the cover section has a three-dimensional shape formed to cover the front of the breast implant. Each of the base section and cover section, are made of a material comprising a plurality of pores for tissue ingrowth. The base section, cover section, or both sections may further comprise one or more connectors that can be used to secure the base section and cover section around the breast implant to form the wrap.

In embodiments, the breast implant fixation device comprises a wrap that is at least partially formed of one or more elastic materials, preferably wherein the cover section of the wrap has a higher elasticity than that of the base section of the wrap. More preferably, the elasticity of the cover section of the wrap increases from the area in contact with the top of the breast implant to the area in contact with the bottom of the breast implant, when the breast implant is contained in the wrap and placed in the breast. The elasticity of the wrap makes it is easy to wrap the breast implant, and provides a tight conformation of the wrap around the breast implant. The ability of the cover section of the wrap to stretch allows it to drape the convex part of the breast implant.

In embodiments, the breast implant fixation device comprises a two dimensional first configuration comprising a base section, a cover section, and a hinge region connecting the base section to the cover section, and a second three dimensional configuration comprising a shape and size to at least partially cover the breast implant when the cover section is wrapped around the front of the breast implant and secured to the base section, wherein the elasticity of the cover section is greater than the elasticity of the base section. In embodiments, the cover section has an elasticity of 15-75%. In embodiments, the base section has an elasticity of at least 5%, and less than 25% unless the elasticity of the cover section is less than 25% in which case the elasticity of the base section shall preferably be less than the elasticity of the cover section.

In embodiments, the base section and cover section comprise a plurality of pores. In embodiments, the average diameter of the pores in the cover section is smaller than the average diameter of the pores in the base section.

In embodiments, the breast implant fixation device comprises one or more tabs for securing the device in the patient.

In embodiments, the thickness of the cover section of the device is greater than the thickness of the base section of the device. In embodiments, the base section of the device is formed from a first mesh, and the cover section is formed from a second mesh. In embodiments, the elasticity of the second mesh is greater than the elasticity of the first mesh.

In embodiments, the breast implant fixation device comprises fibers in the base section and cover section, and the average diameter of the fibers in the base section is larger than the average diameter of the fibers in the cover section.

In embodiments, the breast implant fixation device comprises a wrap with cover and base sections, and the cover section of the wrap is thicker than the base section of the wrap. When the wrap containing the breast implant is placed in the breast, the cover section is located between the patient's skin and the breast implant, and minimizes the formation of ripples or indentations on the patient's skin and reduces palpability of the breast implant.

In embodiments, the breast implant fixation device comprises a wrap that is formed from a textile, woven textile, knitted textile, non-woven textile, monofilament mesh, multifilament mesh, or dry spun textile.

In another embodiment, the breast implant fixation device comprises a wrap comprising a base section for placement on the chest wall of the patient, a bottom cover section for placement in the front lower pole of the breast, a top cover section for placement in the front upper pole of the breast, and an intermediate cover region between the bottom cover section and top cover section for placement under the skin of the patient; and the wrap is porous in order to allow tissue in-growth and limit movement of the breast implant.

In embodiments, the breast implant fixation device comprises a wrap, and one of the mechanical properties selected from the group consisting of porosity, thickness, and elasticity vary along the wrap's cover section from the area that is located in the upper pole of the breast to the area that is located in the lower pole of the breast.

In embodiments, the breast implant fixation device comprises a wrap, and the porosity of the wrap is adjusted to facilitate wrapping the breast implant in the wrap, particularly when the breast implant is round. In embodiments, the breast implant fixation device includes larger pores in the base of the wrap to provide a less dense wrap that is more drapable. In embodiments, the breast implant fixation device includes smaller pores in the cover section of the wrap to increase the surface area of the cover section of the wrap relative to the base of the wrap, and to increase the surface area that is able to hold or be coated with fat.

In embodiments, a method includes the step of applying fat to the cover of the wrap, and in a particular embodiment, autologous fat is applied or otherwise provided on the front of the wrap prior to implantation.

In embodiments, the breast implant fixation device comprises a wrap that can be shaped around a breast implant to prevent movement of the breast implant wherein the wrap is adapted to engage the breast implant preventing the breast implant from substantially rotating inside the wrap; and wherein the wrap further comprises a plurality of outwardly extending (or protruding) anchors, and wherein the anchors are characterized by fibrous or filament-type construction, and optionally, wherein the density of the anchors ranges from 10-50 anchors per square cm, and optionally, 20-30 anchors per square cm.

In embodiments, a breast implant wrap for limiting movement of the breast implant in a patient comprises a thin sheet-like two dimensional first configuration. The first configuration further comprises a base section, a cover section, and a hinge region connecting the base section to the cover section. The wrap further comprises a second three-dimensional configuration having a shape and size to at least partially cover the breast implant when the cover section is folded around the front of the breast implant and secured to the base section. In embodiments, the cover section has a profile selected from the group consisting of: star, flower, and gear.

In view of the foregoing, it is thus an object of the invention to provide medical devices, e.g. wraps, for use with breast implants that limit movement, including migration and rotation, of the breast implants.

It is still another object of the invention to provide breast implant fixation devices that limit migration of breast implants, prevent the breast implant from being palpable, and prevent the formation of any ripples or indentations when breast implants are placed in the breast.

It is a further object of the invention to provide breast implant fixation devices that reduce capsular contraction.

It is yet another object of the invention to provide methods to prepare or manufacture wraps that limit movement of breast implants.

It is still another object of the invention to provide methods to implant the wraps and breast implants.

These and other objects, aspects, and advantages of the subject invention shall become apparent in view of the following description with reference to the accompanying figures.

DETAILED DESCRIPTION OF THE INVENTION

Figure 1C:
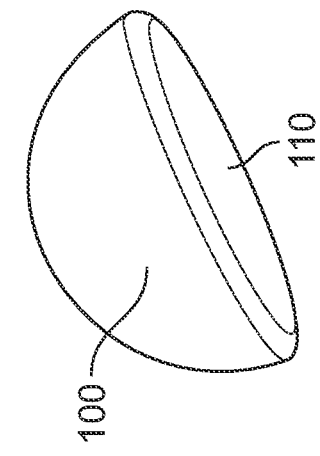
FIGS. 1A-1D show a back view, front view, bottom side perspective view, and side view in situ, respectively, of a breast implant (100) where the back (110) of the breast implant is placed on the chest wall (150) of the patient, and the front (120) of the breast implant is placed just beneath the skin of the patient. The top side (130) of the breast implant is placed in the upper pole (160) of the breast, and the bottom side (140) of the breast implant is placed in the lower pole (170) of the breast.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

In embodiments of the invention, an implantable medical device limits movement of an implanted breast implant, maintains the patient's physical appearance, reduces or eliminates breast implant palpability, and decreases the chances of capsular contraction and the development of breast-implant associated lymphoma. The medical device used to prevent or limit migration and rotation of a breast implant can be made for use with a wide variety of types of breast implants, and used in breast reconstruction procedures following mastectomy as well as breast augmentation procedures, including augmentation mastopexy procedures.

In embodiments, the medical device is a wrap, and is utilized by at least partially wrapping the breast implant inside the wrap and securing the breast implant inside the wrap. Preferably, the breast implant cannot rotate more than 45 degrees inside the wrap, and more preferably the breast implant cannot rotate more than 30 degrees inside the wrap. After securing the breast implant inside the wrap, the wrap containing the breast implant is then implanted in the breast by the surgeon. Movement of the breast implant is prevented after implantation by tissue growth into the wrap which anchors or fixates the wrap and therefore the breast implant in place. Preferably, the wrap is made from synthetic polymeric material to reduce the risk of disease transmission associated with human or animal-derived implants.

In embodiments, the medical device is a breast implant fixation device comprising a wrap, and is utilized by wrapping the wrap around the breast implant to at least partially cover the breast implant. The wrap is porous and allows tissue in-growth. Tissue in-growth fixates the wrap in place and prevents migration of the breast implant. Palpability of the breast implant is reduced or eliminated by the enhanced or optimized thickness of the cover section of the implant which separates the patient's skin and the front of the breast implant. FIGS. 1A-1D show various views of a breast implant with the front, back, top and bottom of the breast implant labelled. The enhanced or optimized thickness of the cover section of the wrap, discussed herein, which covers the front of the breast implant, also reduces or eliminates the appearance of indentations or ripples on the patient's skin due to the presence of the breast implant.

I. Definitions

"Absorbable" as generally used herein means the material is degraded in the body, and the degradation products are eliminated or excreted from the body. The terms "absorbable", "resorbable", "degradable", and "erodible", with or without the prefix "bio", can be used interchangeably herein, to describe materials broken down and gradually absorbed, excreted, or eliminated by the body.

"Average pore size diameter" as used herein is calculated using open source ImageJ software available at https://imagej.nih.gov/ij/index.html.

"Bioactive agent" is used herein to refer to therapeutic, prophylactic or diagnostic agents, preferably agents that promote healing and the regeneration of host tissue, and also therapeutic agents that prevent, inhibit or eliminate infection. "Agent" includes a single such agent and is also intended to include a plurality.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer formed of two or more different monomers.

"Breast implant" as used herein refers to a prosthesis that is implanted in place of a female breast, but can also be implanted to change the size, shape and contour of a woman's breast.

"Burst strength" as used herein is determined by test method ASTM D6797-02 "Standard test method for bursting strength of fabrics constant rate of extension (CRE) ball burst test," using a MTS Q-Test Elite universal testing machine or similar device. The testing fixture uses a ⅜ inch diameter ball.

"Copolymers of poly(butylene succinate)" as generally used herein means any polymer containing 1,4-butanediol units and succinic acid units with one or more different diols, diacid or hydroxycarboxylic acid units, including hydroxycarboxylic acid groups with one or more carboxylic acid or hydroxy acid groups. The copolymers may also comprise chain extenders, coupling agents, cross-linking agents or branching agents.

"Copolymers of poly-4-hydroxybutyrate" as generally used herein means any polymer containing 4-hydroxybutyrate with one or more different hydroxy acid units.

"Elasticity" as used herein is measured as the percent increase of the area of a test article when the area is subject to deformation in ASTM burst method D6797-02 using a round ball.

"Elongation to break" as used herein means the increase in length of a material that occurs when tension is applied to break the material. It is expressed as a percentage of the material's original length.

"Endotoxin units" as used herein are determined using the limulus amebocyte lysate (LAL) assay as further described by Gorbet et al. Biomaterials, 26:6811-6817 (2005).

"Lower pole" as generally used herein means the part of the breast located between the inframammary fold (IMF) and the nipple meridian reference, and protruding away from the chest wall.

"Macro-porous" materials or structures as used herein have average pore size diameters of at least 25 microns, more preferably at least 50 microns, and even more preferably at least 75 microns.

"Molecular weight" as used herein, unless otherwise specified, refers to the weight average molecular weight (Mw), not the number average molecular weight (Mn), and is measured by GPC relative to polystyrene.

"Nipple meridian reference" or "NMR" is the plane drawn horizontally through the nipple to the chest wall.

"Oriented" as generally used herein refers to molecular alignment of polymer chains in a material. A polymer that has been stretched becomes partly oriented and then highly oriented, and the tensile strength increases with increasing orientation. For example, an unoriented polymeric fiber may be stretched to orient the fiber which results in a polymeric fiber with higher tensile strength. An "oriented mesh" means a mesh made with oriented fibers.

"Poly-4-hydroxybutyrate" as generally used herein means a homopolymer containing 4-hydroxybutyrate units. It can be referred to herein as Tepha's P4HB™ polymer or Tepha-FLEX® biomaterial (manufactured by Tepha, Inc., Lexington, Mass.).

"Poly(butylene succinate)" as generally used herein means a polymer containing 1,4-butanediol units and succinic acid units.

"Strength retention" as used herein means the amount of time that a material maintains a particular mechanical property following implantation or exposure to a particular set of conditions. For example, if the stress required to break a multifilament yarn or monofilament fiber after one month is half of its original value then the multifilament or monofilament fiber is said to have a 50% strength retention after one month.

"Suture pullout strength" as used herein means the peak load (kg) at which a breast implant fixation device fails to retain a suture. It is determined using a tensile testing machine by securing the breast implant fixation device in a horizontal plate, threading a suture in a loop through the breast implant fixation device at a distance of 1 cm from the edge of the breast implant fixation device, and securing the suture arms in a fiber grip positioned above the breast implant fixation device. Testing is performed at a crosshead rate of 100 mm/min, and the peak load (kg) is recorded. The suture is selected so that the breast implant fixation device will fail before the suture fails. The suture pullout strength may be converted and expressed as Newtons.

"Tensile modulus" is the ratio of stress to strain for a given material within its proportional limit.

"Tissue expander" ("TE") as used herein means a breast implant that is placed temporarily in the breast to expand tissues and make room for a breast implant. The TE is expanded (e.g., inflated) periodically, for example, by injecting a liquid or gas into the TE. The TE is removed once the tissue has been sufficiently stretched to make room for a permanent breast implant.

"Upper pole" as generally used herein means the top part of the breast located between the nipple meridian reference and the position at the top of the breast where the breast takes off from the chest wall, and protruding away from the chest wall.

II. Materials for Preparing Wraps to Limit Movement of Breast Implants

In accordance with embodiments of the invention described herein, implantable medical devices, namely breast implant fixation devices, limit the movement of breast implants. In particular embodiments, the medical devices are in the form of a wrap sized to enclose the breast implant. In embodiments, the wraps are porous, and fixated in place by tissue in-growth. The wraps anchor at the site of implantation, and in embodiments limit movement of the breast implants by applying compressive or frictional forces to the breast implants. In embodiments, the wraps prevent the breast implants from rotating inside the wraps. In embodiments, the wraps anchor at the site of implantation, and prevent pocket stretch, lateral displacement of the breast implant, and ptosis by preventing or limiting migration of the breast implant. In embodiments, the wraps reduce capsular contraction around the breast implant.

Figure 2:
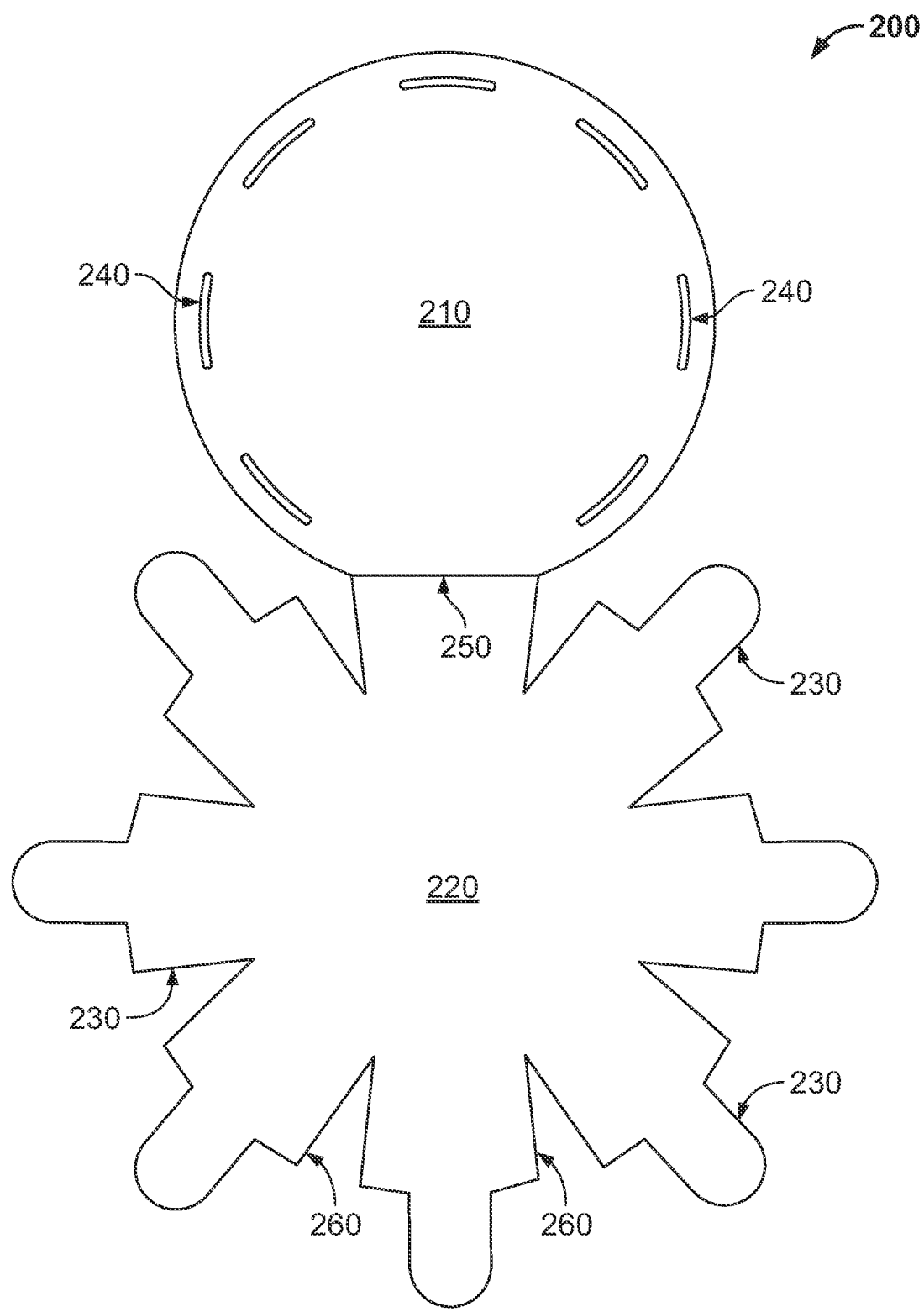
FIG. 2 shows a wrap (200) for a breast implant in accordance with an embodiment of the invention comprising a base section (210) of the wrap, a cover section (220) of the wrap, and a hinge (250) joining sections (210) and (220). The cover section contains tabs (230) that insert into slits (240) in the base section (210) to secure an implant inside the wrap.

With reference to FIG. 2, an embodiment of a wrap (200) in accordance with the subject invention is shown. As described further herein, the wrap (200) is preferably porous, and has a base section (210) for placement on the chest wall of the patient, and a cover section (220) for placement under the skin of the patient. The wrap (200) preferably comprises one or more tabs (230) that can be fastened to secure the breast implant inside the wrap. In embodiments, the tabs (230) can be fastened to the base section of the wrap by inserting them in slits (240) in the base section of the wrap. In embodiments, the cover section (220) of the wrap has a thickness (t) sufficient to hide any ripples or indentations in the patient's skin when a breast implant is placed on the base section (210) of the wrap, and the cover section (220) is draped over the breast implant, secured in place, and the wrap is placed in the patient's breast. The thickness (t) of the wrap is also preferably sufficient to prevent the breast implant from being palpable. An exemplary range for the thickness (t) on the cover section (220) of the wrap is 0.5-10 mm and more preferably from 0.5-3 mm. In embodiments, the cover section (220) of the wrap has a thickness to prevent palpability and the appearance of ripples or indentations on the patient's skin, and the cover section (220) of the wrap is thicker than the base section (210) of the wrap. The thickness (t) of the cover section (220) of the wrap may be uniform. In embodiments, the elasticity of the cover section (220) is greater than the elasticity of the base section (210).

In an alternative embodiment, the wrap comprises separate cover and base sections that the surgeon can assemble to form the device. The wrap may be assembled by placing the breast implant on the base section, and then placing the cover section on the front of the breast implant, or vice versa. The cover and base sections may be joined together to secure the breast implant inside the wrap. The cover and base sections may further comprise connectors to join the cover and base sections together. The cover section preferably has a three-dimensional shape designed to fit over the front of the breast implant. The base section preferably has a two-dimensional shape, but may have a substantially three-dimensional shape with a flat base and concave shaped perimeter. The tabs (230) may also be used for fixation of the wrap to the patient. The sections may further comprise one or more additional tabs to anchor the wrap to the chest wall of the patient, or the surgeon may anchor the sections directly to the chest wall. Preferably the base section is anchored to the chest wall. The wrap preferably has pores sized to allow tissue in-growth. In embodiments, the separate cover section has an elasticity that is higher than the elasticity of the separate base section of the device.

Figure 1B:
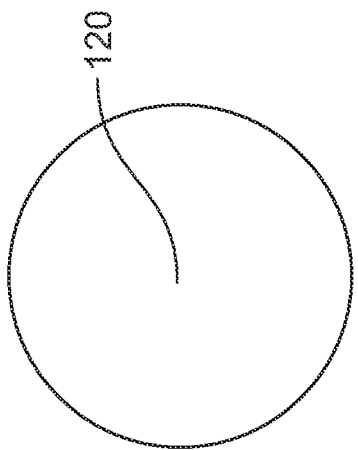
Figure 1A:
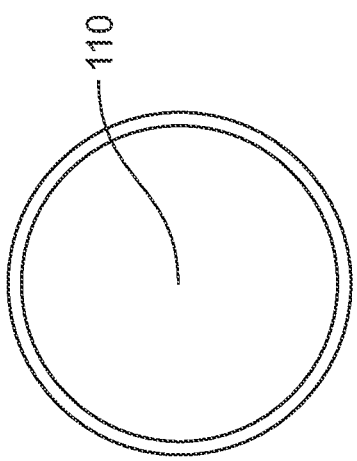
Figure 1D:
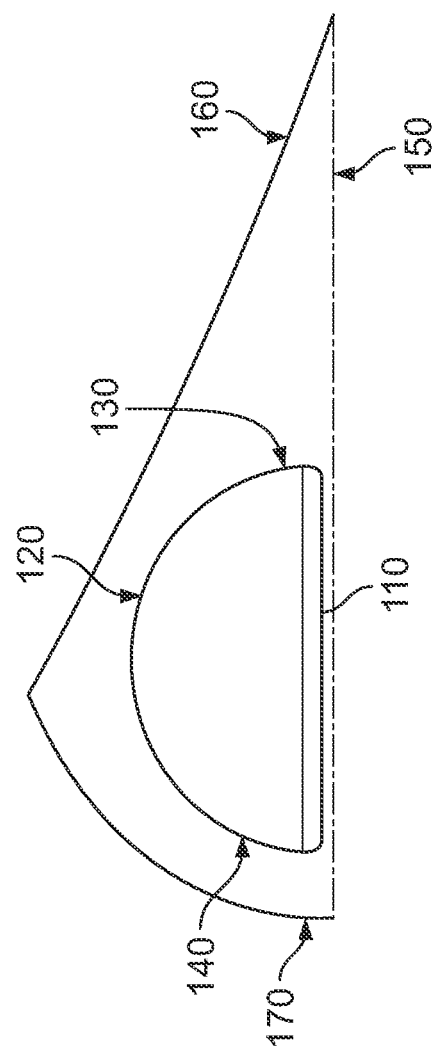

However, in other embodiments, the thickness of the wrap or other mechanical properties described herein vary along the cover section of the wrap from the area in contact with the top side of the breast implant to the area in contact with the bottom side of the breast implant (see FIG. 1B). For example, the thickness of the cover section of the wrap may decrease from the area in contact with the top side of the breast implant to the area in contact with the bottom side of the breast implant. The area of the cover section of the wrap that comes into contact with the top side of the breast implant may have a thickness that is 5-10 times greater than the area of the cover section that comes into contact with the bottom side of the breast implant. Additionally, in a preferred embodiment, the base of the wrap has a thickness less than the cover section of the wrap.

The elasticity may also vary along the regions of the wrap. In embodiments, a wrap has a base section (210) for placement on the chest wall of the patient, and a cover section (220) for placement under the patient's skin, and an elasticity of the cover section (220) of the wrap of 15-75%, and more preferably 30-65%, and an elasticity of the base section (210) of the wrap of 5-25%, and more preferably 8-20% when the elasticities are measured as the percent increases of the sections when the sections are subject to deformation in ASTM burst method D6797-02 using a round ball. In a particularly preferred embodiment, the elasticity of the cover section (220) is 30-65%, and the elasticity of the base section (210) is 5-25%. In embodiments, the elasticity of the cover section (220) is greater than the elasticity of the base section (210). The elasticities of the cover section and base section allow the breast implant to be easily wrapped in the wrap with the wrap conforming tightly to the contours of the breast implant. In embodiments, the device (200) is adapted to be wrapped tightly around the entire implant so that no gaps are present along the entire contour of the implant.

In embodiments, the wraps of the breast implants have different porosities in different regions of the wraps. The porosities of the base section (210) and the cover section (220) of the wraps may be different. The porosity of the cover section (220) may be different in the region that is located in the lower pole of the breast than in the region that is located in the upper pole of the breast.

In embodiments, the wrap has large average pore size diameters on the base section of the wrap (which is placed on the chest wall of the patient), and smaller average pore size diameters on the cover of the wrap (which is placed on the front of the breast implant, and is located between the breast implant and the patient's skin). Smaller average pore size on the cover of the wrap provide greater surface area for holding fat graft. In embodiments, the cover section (220) of the wrap is denser than the base section (210) of the wrap.

In embodiments, the breast implant fixation devices prevent migration of the breast implants by more than 5 cm, and even more preferably by more than 3 cm. In embodiments, the breast implant fixation devices limit rotation of the wrapped breast implant by more than 45 degrees, and more preferably by more than 30 degrees. The wraps partially or completely cover the breast implants. Preferably, the breast implants are wrapped with the wraps prior to implantation. The wraps are preferably porous and allow tissue in-growth. The dimensions of the wraps are tailored to accommodate the size and shape of the breast implant being implanted. The dimensions of the breast implants are selected by the surgeon according to the needs of the patient, and the patient's preferences.

The wraps are preferably made of absorbable polymers. Additionally, the wraps may be made from a single component, such as an unoriented, partially or fully oriented monofilament fiber or fibers, including non-wovens, wovens, and knitted mesh, or from two or more components, such as fibers, textiles or films with different properties. The wraps can optionally comprise bioactive agents, as well as cells, including stem cells. The wraps preferably have a pyrogen level of less than 20 endotoxin units per device, and can be sterilized.

A. Polymers for Preparing Wraps

The wraps may comprise degradable materials, and more preferably are made completely from degradable materials. In a preferred embodiment, the devices for fixation of breast implants are made from one or more absorbable polymers, preferably absorbable thermoplastic polymers and copolymers. The implantable wrap may, for example, be prepared from polymers including, but not limited to, polymers of glycolic acid, lactic acid, 1,4-dioxanone, trimethylene carbonate, 3-hydroxybutyric acid, 4-hydroxybutyric acid, ε-caprolactone, 1,4-butanediol, and succinic acid, including polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly(orthoesters); polyanhydrides; poly(phosphazenes); polyhydroxyalkanoates (PHA's); synthetically or biologically prepared polyesters; polycarbonates; tyrosine polycarbonates; polyamides (including synthetic and natural polyamides, polypeptides, and poly(amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly (lactide), poly(lactide-co-glycolide), or polycaprolactone and copolymers thereof, including random copolymers and block copolymers thereof. Preferably the absorbable polymer or copolymer will be substantially or completely resorbed two years after implantation.

Blends of polymers, preferably absorbable polymers, can also be used to prepare the wraps. Particularly preferred blends of absorbable polymers include, but are not limited to, polymers of glycolic acid, lactic acid, 1,4-dioxanone, trimethylene carbonate, 3-hydroxybutyric acid, 4-hydroxybutyric acid, ε-caprolactone, 1,4-butanediol, succinic acid or copolymers thereof.

In a particularly preferred embodiment, the wraps comprise poly-4-hydroxybutyrate (Tepha's P4HB™ polymer, Lexington, Mass.) or a copolymer thereof, and may in one embodiment be made completely with P4HB or copolymer thereof. Copolymers include P4HB with another hydroxyacid, such as 3-hydroxybutyrate, and P4HB with glycolic acid or lactic acid monomer. P4HB is a strong, pliable thermoplastic polyester that is biocompatible and resorbable (Williams, et al. Poly-4-hydroxybutyrate (P4HB): a new generation of resorbable medical devices for tissue repair and regeneration, Biomed. Tech. 58(5):439-452 (2013)). Upon implantation, P4HB hydrolyzes to its monomer, and the monomer is metabolized via the Krebs cycle to carbon dioxide and water. In a preferred embodiment, the P4HB homopolymer and copolymers thereof have a weight average molecular weight, Mw, within the range of 50 kDa to 1,200 kDa (by GPC relative to polystyrene) and more preferably from 100 kDa to 600 kDa. A weight average molecular weight of the polymer of 50 kDa or higher is preferred for processing and mechanical properties.

In another preferred embodiment, the wraps comprise a polymer comprising at least a diol and a diacid. In a particularly preferred embodiment, the polymer used to prepare the wrap is poly(butylene succinate) (PBS) wherein the diol is 1,4-butanediol and the diacid is succinic acid. The poly(butylene succinate) polymer may be a copolymer with other diols, other diacids or a combination thereof. For example, the polymer may be a poly(butylene succinate) copolymer that further comprises one or more of the following: 1,3-propanediol, 2,3-butanediol, ethylene glycol, 1,5-pentanediol, glutaric acid, adipic acid, terephthalic acid, malonic acid, methylsuccinic acid, dimethylsuccinic acid, and oxalic acid. Examples of preferred copolymers are: poly(butylene succinate-co-adipate), poly(butylene succinate-co-terephthalate), poly(butylene succinate-co-butylene methylsuccinate), poly(butylene succinate-co-butylene dimethylsuccinate), poly(butylene succinate-co-ethylene succinate) and poly(butylene succinate-co-propylene succinate). The poly(butylene succinate) polymer or copolymer may also further comprise one or more of the following: chain extender, coupling agent, cross-linking agent and branching agent. For example, poly(butylene succinate) or copolymer thereof may be branched, chain extended, or cross-linked by adding one or more of the following agents: malic acid, trimethylol propane, trimesic acid, citric acid, glycerol propoxylate, and tartaric acid. Particularly preferred agents for branching, chain extension, or crosslinking the poly(butylene succinate) polymer or copolymer thereof are hydroxycarboxylic acid units. Preferably the hydroxycarboxylic acid unit has two carboxylic groups and one hydroxyl group, two hydroxyl groups and one carboxyl group, three carboxyl groups and one hydroxyl group, or two hydroxyl groups and two carboxyl groups. In one preferred embodiment, the wrap comprises poly(butylene succinate) comprising malic acid as a branching, chain extending, or cross-linking agent. This polymer may be referred to as poly(butylene succinate) cross-linked or chain-extended with malic acid, succinic acid-1,4-butanediol-malic acid copolyester, or poly(1,4-butylene glycol-co-succinic acid), cross-linked or chain-extended with malic acid. It should be understood that references to malic acid and other cross-linking agents, coupling agents, branching agents and chain extenders include polymers prepared with these agents wherein the agent has undergone further reaction during processing. For example, the agent may undergo dehydration during polymerization. Thus, poly(butylene succinate)-malic acid copolymer refers to a copolymer prepared from succinic acid, 1,4-butanediol and malic acid. In another preferred embodiment, malic acid may be used as a branching, chain-extending or cross-linking agent to prepare a copolymer of poly(butylene succinate) with adipate, which may be referred to as poly[(butylene succinate)-co-adipate] cross-linked or chain-extended with malic acid. As used herein, "poly(butylene succinate) and copolymers" includes polymers and copolymers prepared with one or more of the following: chain extenders, coupling agents, cross-linking agents and branching agents. In a particularly preferred embodiment, the poly(butylene succinate) and copolymers thereof contain at least 70%, more preferably 80%, and even more preferably 90% by weight of succinic acid and 1,4-butanediol units. The polymers comprising diacid and diols, including poly(butylene succinate) and copolymers thereof and others described herein, preferably have a weight average molecular weight (Mw) of 10,000 Da to 400,000 Da, more preferably 50,000 Da to 300,000 Da and even more preferably 100,000 Da to 200,000 Da based on gel permeation chromatography (GPC) relative to polystyrene standards. In a particularly preferred embodiment, the polymers and copolymers have a weight average molecular weight of 50,000 Da to 300,000 Da, and more preferably 75,000 Da to 300,000 Da. In one preferred embodiment, the poly(butylene succinate) or copolymer thereof used to make the wrap, or a component of the wrap, has one or more, or all of the following properties: density of 1.23-1.26 g/cm$^3$, glass transition temperature of −31° C. to −35° C., melting point of 113° C. to 117° C., melt flow rate (MFR) at 190° C./2.16 kgf of 2 to 10 g/10 min, and tensile strength of 30 to 60 MPa.

B. Additives

Certain additives may be incorporated into the wraps, preferably in the absorbable polymer, copolymer or blends thereof that are used to make the wrap. Preferably, these additives are incorporated during a compounding process to produce pellets that can be subsequently melt-processed. For example, pellets may be extruded into fibers suitable for making the wraps. In another embodiment, the additives may be incorporated using a solution-based process, for example, fibers may be spun from solutions of the polymer and one or more additives. In a preferred embodiment, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts between 1% and 20% by weight. Nucleating agents may be incorporated to increase the rate of crystallization of the polymer, copolymer or blend. Such agents may be used, for example, to facilitate fabrication of the wrap, and to improve the mechanical properties of the wrap. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the compositions for preparing the wraps include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

C. Bioactive Agents

The wraps can be loaded or coated with bioactive agents. Bioactive agents may be included in the wraps for a variety of reasons. For example, bioactive agents may be included in order to improve tissue in-growth into the wrap, to improve tissue maturation, to provide for the delivery of an active agent, to improve wettability of the implant, to prevent infection, and to improve cell attachment.

The wraps may contain cellular adhesion factors, including cell adhesion polypeptides. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, laminin, elastin, fibrinogen, collagen types I, II, and V, as well as synthetic peptides with similar cell adhesion properties. The cell adhesion polypeptides also include peptides derived from any of the aforementioned proteins, including fragments or sequences containing the binding domains.

The wraps can incorporate wetting agents designed to improve the wettability of the surfaces of the wrap to allow fluids to be easily adsorbed onto the wrap surfaces, and to promote cell attachment and or modify the water contact angle of the wrap surface. Examples of wetting agents include polymers of ethylene oxide and propylene oxide, such as polyethylene oxide, polypropylene oxide, or copolymers of these, such as PLURONICS®. Other suitable wetting agents include surfactants or emulsifiers.

The wraps can contain gels, hydrogels or living hydrogel hybrids to further improve wetting properties and to promote cellular growth throughout the thickness of the scaffold. Hydrogel hybrids consist of living cells encapsulated in a biocompatible hydrogel like gelatin, silk gels, and hyaluronic acid (HA) gels.

The wraps can contain active agents designed to stimulate cell in-growth, including growth factors, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1 B), interleukin-8 (IL-8), and nerve growth factor (NGF), and combinations thereof.

Other bioactive agents that can be incorporated in the wraps include antimicrobial agents, in particular antibiotics, disinfectants, oncological agents, anti-scarring agents, anti-inflammatory agents, anesthetics, small molecule drugs, anti-angiogenic factors and pro-angiogenic factors, immunomodulatory agents, and blood clotting agents. The bioactive agents may be proteins such as collagen and antibodies, peptides, polysaccharides such as chitosan, alginate, hyaluronic acid and derivatives thereof, nucleic acid molecules, small molecular weight compounds such as steroids, inorganic materials such as hydroxyapatite, or complex mixtures such as platelet rich plasma. Suitable antimicrobial agents include: bacitracin, biguanide, triclosan, gentamicin, minocycline, rifampin, vancomycin, cephalosporins, copper, zinc, silver, and gold. Nucleic acid molecules may include DNA, RNA, siRNA, miRNA, antisense or aptamers.

The wraps may also comprise allograft material and xenograft materials, including acellular dermal matrix material and small intestinal submucosa (SIS).

In yet another preferred embodiment, the wraps may incorporate systems for the controlled release of the therapeutic or prophylactic agents.

D. Fibers

The wraps may comprise fibers. The fibers are preferably made from degradable thermoplastic polymers, and even more preferably from degradable thermoplastic polyesters. The fibers are preferably made from the degradable materials listed in section II.A above. In a preferred embodiment, the fibers are made from P4HB or copolymer thereof. In another preferred embodiment, the fibers are made from poly(butylene succinate) or copolymer thereof. The fibers may be monofilament fibers, multifilament fibers, or combinations thereof. The fibers may be a yarn that is twisted, not twisted, or substantially parallel strands. The fibers may be unoriented, partially oriented, highly oriented or combinations thereof. Preferably, the fibers are highly oriented. The fibers may have elongation to break values of 3% to 1,100%, and more preferably from 10% to 100%. The fibers may have diameters ranging from 1 µm to 5 mm, more preferably from 10 µm to 1 mm, and even more preferably from 20 µm to 750 µm. The fibers in the wrap may have different weight average molecular weights. Preferably the polymers of the fibers have weight average molecular weights of 10 kDa to 1,200 kDa, but more preferably 50 kDa to 600 kDa. The fibers in the wrap may have different tensile strengths. Preferably, the tensile strength of the fibers in the wrap is 300-1,300 MPa. The fibers in the wrap are preferably flexible. Preferably, the fibers in the wrap have a tensile modulus of 70-1,000 MPa, and more preferably 400-1,000 MPa. The fibers may have short strength retention profiles, prolonged strength retention profiles, or combinations thereof. In one embodiment, a short strength retention profile is 1 to 12 weeks, and a prolonged strength retention profile is 4 months to 5 years, more preferably 4 months to 2 years. The fibers of the wrap may have different degradation rates in vivo. Some fibers may degrade quickly while other fibers may degrade slowly. In another embodiment, the fibers comprise an additive or bioactive agent. The fibers can be produced by any suitable method but melt extrusion or solvent spinning are preferred. In embodiments, the breast implant fixation device has a base section and a cover section, and the average size of the fibers in the base section is larger than the average size of the fibers in the cover section.

In a preferred embodiment, the fiber is made from P4HB monofilament fiber. Suitable P4HB monofilament filament fibers can be produced by melt extrusion using the following method. Bulk P4HB resin in pellet form is dried to less than 300 ppm water using a rotary vane vacuum pump system. The dried resin is transferred to an extruder feed hopper with nitrogen purge to keep the pellets dry. The pellets are gravity fed into a chilled feeder section and introduced into the extruder barrel, which is 1.50 inches (3.81 cm) in diameter and fitted with an extrusion screw with a 30:1 L/D ratio. The extruder barrel contains 5 heating zones (or extrusion zones)—zones 1, 2, 3, 4 and 5. A suitable extruder is manufactured by American Kuhne. The heated and softened resin from the extruder is fed into a heated metering pump (melt pump) and from the melt pump the extruded resin is fed into the heated block and an eight-hole spinneret assembly. Processing profile ranges from 40° C. to 260° C. for temperatures, and 400 psi to 2000 psi for pressures, are used. The molten filaments are water quenched and conveyed into a three-stage orientation, with inline relaxation, before winding of the monofilaments on spools. Typical test values for extruded monofilament fiber are shown in Table 1.

TABLE 1

Mechanical Test Data for P4HB Monofilament Fiber

| Diameter, mm | Breaking Strength, Kgf | Break Elongation |
|---|---|---|
| 0.165 | 1.80 | 26% |
| 0.150 | 1.80 | 30% |
| 0.100 | 1.00 | 29% |

In another preferred embodiment, the fiber is made from poly(butylene succinate) or copolymer thereof. Suitable monofilament fibers of poly(butylene succinate) or copolymer thereof can be produced by melt extrusion.

Wraps that can prevent rotation and migration of breast implants can be prepared from the fibers described above. Such wraps can be produced from slow and fast degrading fibers, degradable fibers of different molecular weights, fibers that are unoriented, partially oriented and fully oriented, fibers with different elongation to break values, tensile strengths and tensile modulus values, or combinations thereof.

E. Films

The wraps may comprise films, and more preferably films that have been perforated to make them porous. The pores of the perforated films preferably have pore diameters from 0.01 mm to 10 mm, and more preferably from 0.1 mm to 1 mm. In a particularly preferred embodiment, the perforated films have pores that are larger than 0.5 mm, even more preferably at least 0.8 mm. The density of the pores of the perforated films is preferably greater than 1 per square cm, but less than 50 per square cm. The films are preferably made from degradable thermoplastics, and even more preferably from degradable polyesters. The films are preferably made from the degradable materials listed in Section II.A above. In a preferred embodiment, the films are made from P4HB or copolymer thereof, or from poly(butylene succinate) or copolymer thereof. The weight average molecular weight of the polymers in the films is preferably 10 kDa to 1,200 kDa, but is more preferably 50 kDa to 600 kDa. The films may be unoriented, partially oriented, mono-axially oriented or bi-axially oriented. The elongation to break of the films can be from 3-1,100%, but is more preferably 15%-300%. The thickness of the films is preferably from 0.01 mm to 10 mm. The burst strength of the films, including the perforated films, is preferably from 1-100 Kgf. The films may have short strength retention profiles, prolonged strength retention profiles, or combinations thereof. In one embodiment, a short strength retention profile is 1 to 12 weeks, and a prolonged strength retention profile is 4 months to 5 years, more preferably 4 months to 2 years. The films of the wrap may have different degradation rates in vivo. Some films may degrade quickly while other films may degrade slowly. In another embodiment, the films comprise an additive or bioactive agent. The films can be produced by any suitable method, including melt extrusion, compression molding, injection molding, and solvent casting. In another embodiment, the films may be laminated or thermoformed. In one embodiment, the films may be laminated and then the laminated article perforated and used to form a wrap. In embodiments, the breast implant fixation device comprises a base section and a cover section, wherein the base section comprises a first film and the cover section comprises a second film, and the elasticity of the second film is greater than the elasticity of the first film.

Wraps that can prevent or limit migration and rotation of breast implants can be prepared from the films described above. Such wraps can be produced from slow and fast degrading films, films of different molecular weights, films with different degrees of orientation, films of different thicknesses, and films that are perforated, laminated or thermoformed, or combinations thereof.

F. Foams

The wraps may comprise foams. The foams are preferably made from degradable thermoplastic polymers, and even more preferably from degradable thermoplastic polyesters. The foams are preferably made from the degradable materials listed in Section II.A above. The foams can be made by any suitable method, including melt foaming and solution foaming, including particulate leaching. In a preferred embodiment, the foams are made from P4HB or copolymer thereof or poly(butylene succinate) or copolymer thereof. The foams may optionally be cross-linked. Preferably the polymers of the foams have weight average molecular weights of 10 kDa to 1,200 kDa, but more preferably 50 kDa to 600 kDa. The foams may have open cell or closed cell structures. In one embodiment, the foams have an open cell content of at least 10%, preferably at least 25%, and more preferably at least 50%. The cell sizes may be up to 5 mm. The densities of the foams are preferably less than 1 g/cm$^3$, more preferably less than 0.75 g/cm$^3$, and even more preferably less than 0.5 g/cm$^3$. The thicknesses of the foams may be from 0.01 mm to 10 mm. The foams may comprise additives or bioactive agents. The foams may have short strength retention profiles, prolonged strength retention profiles, or combinations thereof. In one embodiment, a short strength retention profile is 1 to 12 weeks, and a prolonged strength retention profile is 4 months to 5 years, more preferably 4 months to 2 years. In another embodiment, the foams comprise an additive or bioactive agent. In embodiments, the breast implant fixation device comprises a base section and a cover section, wherein the base section comprises a first foam and the cover section comprises a second foam, and the elasticity of the second foam is greater than the elasticity of the first foam.

Wraps that can prevent or limit migration or rotation of breast implants can be prepared from the foams described above. Such wraps can be produced from foams with open or closed cell structures, varying cell sizes and densities, different molecular weights, and different strength retention profiles.

G. Textiles

The wraps may comprise textiles. The textiles are preferably made from degradable thermoplastic polymers, and even more preferably from degradable thermoplastic polyesters. The textiles are preferably made from the degradable materials listed in Section II.A above. In a preferred embodiment, the textiles are made from P4HB or copolymer thereof, or poly(butylene succinate) and copolymers thereof.

The thicknesses of the textiles may be from 0.01 mm to 10 mm. The textiles preferably have an average pore size diameter from 75 µm to 5 mm, but more preferably from 500 µm to 5 mm, and even more preferably from 800 µm to 5 mm. Preferably the polymers and fibers used to make the textiles have weight average molecular weights of 10 kDa to 1,200 kDa, but more preferably 50 kDa to 600 kDa. The burst strength of the textiles is preferably 0.1 Kgf to 100 Kgf, but more preferably 1 Kgf to 50 Kgf. In embodiments, the textiles may have an elasticity of 15-75%, 30-65%, 8-20%, or 5-25%, wherein the elasticity is measured as the percent increase of an area of the textile when the area is subject to deformation in ASTM burst method D6797-02. The textiles may have short strength retention profiles, prolonged strength retention profiles, or combinations thereof. In one embodiment, a short strength retention profile is 1 to 12 weeks, and a prolonged strength retention profile is 4 months to 5 years, more preferably 4 months to 2 years. The wrap may be formed from more than one textile, and the textiles used to form the wrap may degrade at different rates. In embodiments, the breast implant fixation device comprises a base section and a cover section, wherein the base section comprises a first textile and the cover section comprises a second textile, and the elasticity of the second textile is greater than the elasticity of the first textile.

The wraps may be formed from woven and knitted textiles, or may be formed from non-woven textiles.

Woven and Knitted Textiles

In one embodiment, the textiles may be produced from monofilament fibers, multifilament fiber, yarn, or combinations thereof. The textiles may be produced from the fibers described in Section II.D above. The fibers may be unoriented, partially oriented, highly oriented or combinations thereof. The textiles may be knitted, woven, or braided from the fibers. The textiles may also be made from the fibers by crocheting. A particularly preferred textile for use in preparing the wraps is a warp knit mesh. In embodiments, the textiles with a thickness of 0.5-10 mm may be used to make the cover section (e.g. 220) of a wrap. In another embodiment, textiles with a thickness of 0.2-0.6 mm may be used to make the base section (e.g. 210) of a wrap. In another embodiment, textiles with an elasticity of 15-75% or 30-65% may be used to prepare the cover section (e.g. 220) of the wrap, and textiles with an elasticity of 5-25% or 8-20% may be used to prepare the base section (e.g. 210) of a wrap, wherein the elasticity is measured as the percent increase of the area of the section when the area is subject to deformation in ASTM burst method D6797-02 using a round ball. In embodiments, the elasticity of the textile used to prepare the cover section (e.g. 220) of the wrap is greater than the elasticity of the textile used to prepare the base section (e.g. 210) of the wrap.

In other embodiments, the wraps formed from textiles used to make the base sections (e.g. 210), and cover sections (e.g. 220) surrounding the front top and front bottom areas of the breast implant (see FIGS. 1A, 1B respectively) have average pore diameter ranges of 0.5-3 mm, 0.5-1 mm, and 0.1-1 mm, wherein the area of the wrap surrounding the front bottom of the breast implant is placed in the lower pole nearest to the patient's skin, and the area of the wrap surrounding the front top of the breast implant is placed in the upper pole nearest to the patient's skin.

In a preferred embodiment, the textile is a mesh made from P4HB monofilament fiber, or fiber comprising poly(butylene succinate) or copolymer. The P4HB monofilament fiber or fiber comprising poly(butylene succinate) or copolymer thereof may be oriented. In a more preferred embodiment, the P4HB monofilament mesh or mesh comprising poly(butylene succinate) or copolymer thereof, has a knitted or woven structure, and even more preferably is a warp knitted mesh. A particularly preferred P4HB monofilament mesh has substantially one or more of the following properties: an average pore diameter of 500 µm to 3 mm, a pore diameter of approximately 500-1,000 µm, thickness of 0.2-10 mm, 0.2-5 mm, or 0.4-0.8 mm, areal density of 40-190 g/m$^2$ or approx. 140-190 g/m$^2$, suture pullout strength of 1-7 kgf, or 4-7 kgf, and a burst strength of 20-26 Kg or 0.1-30 kgf/cm$^2$. A preferred mesh comprising poly(butylene succinate) or copolymer thereof, has one or more of the following properties: (i) a suture pullout strength of at least 10 N, 1-7 kgf, or at least 20 N, (ii) a burst strength of 0.1 to 100 kgf, more preferably between 1 to 50 kgf, or greater than 0.1 kPa, (iii) a thickness of 0.5-10 mm, more preferably between 0.05-5 mm, (iv) an areal density of 5 to 800 g/m$^2$, (v) a pore diameter of 5 µm to 5 mm, or more preferably 100 µm to 1 mm, or (vi) an average pore diameter of 0.1-3 mm. The textiles comprising P4HB monofilament mesh or poly(butylene succinate) or copolymer thereof with an elasticity of 15-75% or 30-65% may be used to prepare the cover sections (e.g. 220) of the wraps, and textiles comprising these polymers with an elasticity of 5-25% or 8-20% may be used to prepare the base sections (e.g. 210) of the wraps, wherein the elasticity is measured as the percent increase of the cover or base section area when the area is subject to deformation in ASTM burst method D6797-02 using a round ball. In embodiments, the P4HB textile or poly(butylene succinate) textile used to prepare the cover section (e.g. 220) of the wrap has a higher elasticity than the P4HB textile or poly(butylene succinate) textile used to prepare the base section (e.g. 210) of the wrap. A more preferred mesh comprising poly(butylene succinate) or copolymer thereof, has one or more of the following properties: (i) a suture pullout strength of 1 kgf to 20 kgf or 1-7 kgf, (ii) a burst strength of 1 to 50 kgf, more preferably 5 to 30 kgf, and even more preferably 0.1-30 kgf/cm$^2$ (iii) a thickness of 0.2-0.6 mm, 0.5-10 mm, or 0.1 to 1 mm, (iv) areal density of 40-190 g/m$^2$ or 100 to 300 g/m$^2$, and (v) pore diameter 100 µm to 1 mm. An even more preferred mesh comprising poly(butylene succinate) or copolymer thereof, has one or more of the following properties: a pore diameter of 500±250 µm, thickness of 0.4±0.3 mm, areal density of approx. 182±50 g/m$^2$, suture pullout strength of 5.6±2 kgf, and a burst strength of at least 3 kgf, and more preferably at least 6 kgf. A preferred textile comprising poly(butylene succinate) or copolymer thereof is a monofilament knitted mesh, and even more preferably is a warp knit monofilament mesh.

Suitable P4HB monofilament meshes for preparing the wraps may be prepared according to the following procedure: P4HB Monofilament fibers from 49 spools, prepared as described in Section II. D, are mounted on a creel, aligned side by side and pulled under uniform tension to the upper surface of a "kiss" roller. The "kiss" roller is spun while semi-immersed in a bath filled with a 10% solution of TWEEN® 20 lubricant. The TWEEN® 20 lubricant is deposited on the surface of the sheet of fiber. Following the application of TWEEN® 20, the sheet of fiber is passed into a comb guide and then wound on a warp beam. A warp is a large wide cylinder onto which individual fibers are wound in parallel to provide a sheet of fibers. Next, warp beams are converted into a finished mesh fabric by means of interlocking knit loops. Eight warp beams are mounted in parallel onto tricot machine let-offs and fed into the knitting elements at a constant rate determined by the 'runner length'. Each individual monofilament fiber from each beam is fed through a series of dynamic tension elements down into the knitting 'guides'. Each fiber is passed through a single guide, which is fixed to a guide bar. The guide bar directs the fibers around the needles forming the mesh fabric structure. The mesh fabric is then pulled off the needles by the take down rollers at a constant rate of speed determined by the fabric 'quality'. The mesh fabric is then taken up and wound onto a roll ready for scoring. The P4HB monofilament mesh produced according to this method is scored ultrasonically with water, heat set in hot water, and then washed with a 70% aqueous ethanol solution. A similar procedure may be used to prepare a monofilament mesh of poly(butylene succinate) or copolymer thereof.

Non-Woven Textiles

In another embodiment, the textiles may be produced directly from the degradable materials listed in Section II.A. In one preferred embodiment, the textiles have a non-woven structure. More preferably, the non-woven structure is dry-spun. Suitable methods to produce the textiles directly from degradable materials, preferably thermoplastic polymers and thermoplastic polyesters, include melt blowing, electrospinning, centrifugal spinning, spun bonding, and solvent spinning, including dry spinning. Dry spinning is a particularly preferred method for producing the textiles. The textiles may comprise an additive or bioactive agent. Dry spun textiles have a non-woven structure, as well as textiles produced by melt blowing, electrospinning, centrifugal spinning, spun bonding, and dry spinning.

In another preferred embodiment, the textile is a non-woven made from P4HB, or poly(butylene succinate) or copolymer thereof, preferably by solution spinning (also known as dry spinning). Suitable dry spun fibers of P4HB, or poly(butylene succinate) or copolymer thereof, may be produced by dissolving P4HB or poly(butylene succinate) or copolymer thereof, in a solvent to form a polymer solution. Suitable solvents include chloroform, methylene chloride, acetone, and THF. A particularly suitable polymer solution for P4HB is an 8% w/v solution of P4HB in chloroform. The polymer solution may be transferred to a solvent reservoir connected to a nozzle that is aimed at a collector. Dry spun fibers are collected when the polymer solution is injected or pumped into a stream of accelerated gas exiting the nozzle. Suitable dry spun equipment has an inner and a concentric outer nozzle, which creates a low-pressure region near the orifice of the inner nozzle. A suitable gas is compressed air. The collector may be stationary, and the nozzle moved in order to form a non-woven at the collector. However, more preferably, the collector can be rotated and moved in all directions in order for the collector to be completely covered by dry spun fiber, and if desired, to form a uniform coating of dry spun fibers on the collector. Generally, however, the distance between the collector and the nozzle is not varied significantly. In one embodiment, the dry spun fibers have average diameters ranging from 0.01 μm to 50 μm. A particular advantage of solvent spinning P4HB fibers, and fibers of poly(butylene succinate) and copolymers thereof, rather than melt spinning, is that the weight average molecular weight of the polymer does not decrease by more than 10%, and even more preferably does not decrease by more than 5%, during spinning.

Textile Compositions and Properties

Wraps that can limit or prevent migration or rotation of breast implants can be prepared from the woven, knitted and non-woven textiles described above. Such wraps can be produced from slow and fast degrading textiles, woven and non-woven textiles, knitted textiles, warp knitted textiles, degradable textiles of different molecular weights, textiles made from unoriented, partially oriented and fully oriented fibers, textiles made from monofilament fiber, multifilament fiber, yarn, and combinations thereof, textiles made directly from degradable materials, including by electrospinning, melt-blowing, solvent spinning including dry spinning, centrifugal spinning and spun-bonding, and textiles with different burst strengths, or combinations of the above.

In one embodiment, the wrap comprises an auxetic structure, and preferably an auxetic mesh.

In one embodiment, the textile may comprise a bioactive agent. The bioactive agent may be coated on the textile, the bioactive agent may be contained within the textile, or a combination thereof. In a preferred embodiment, the bioactive agent may be applied to the textile by spraying the textile with a solution of the bioactive agent or dip coating the textile in a solution of the bioactive agent. In another preferred embodiment, the textile comprising the bioactive agent may be formed directly in one step. For example, a solution of polymer and bioactive agent may be solution spun, dry spun or electrospun to form a textile comprising the bioactive agent. In a particularly preferred embodiment, the wrap may be formed from a P4HB textile, or textile of poly(butylene succinate) or copolymer thereof, coated with one or more bioactive agents, or by forming the P4HB textile, or textile of poly(butylene succinate) or copolymer thereof, comprising the one or more bioactive agents in one step, for example, by melt or solution processing, dry spinning, solvent spinning, centrifugal spinning, spun-bonding, melt-blowing, melt spinning or electrospinning. In a preferred embodiment, the textile used to form the wrap is a P4HB textile, or textile of poly(butylene succinate) or copolymer thereof, comprising one or more antibiotics.

III. Methods of Manufacturing Wraps to Limit Movement of Breast Implants

A variety of methods can be used to manufacture the breast implant fixation wrap devices, and several different examples of wraps to limit migration and rotation of breast implants are described herein. The wraps limit migration of breast implants after the breast implant is wrapped in the wrap, and the wrap containing the breast implant is implanted in the patient. Limiting migration means that the wrap can be used to prevent the breast implant from migrating a threshold distance after implantation. In embodiments, the threshold distance is 5 cm, and more preferably 3 cm or 1 cm. Prevention of migration is important to prevent pocket stretch, ptosis, and lateral displacement of breast implants. In other embodiments, the wraps limit the rotation of breast implants after implantation in the patient. In embodiments, wraps prevent breast implants from rotating more than 45 degrees, and more preferably more than 30 degrees, after implantation.

The wraps may have a two-dimensional shape that can be formed into a three-dimensional shape when the wrap is wrapped around the breast implant.

In embodiments, a wrap is provided as a flexible planar member and is pocketless, pouch-less, and generally lacks any sort of internal cavity or chamber to receive a breast implant.

In embodiments, wraps may have a three-dimensional shape. The wraps are preferably dimensioned so that they at least partially cover and secure the breast implant. Preferably, the cover section of the wrap is designed to fit closely to the front of the breast implant.

In embodiments, the base section is planar and the cover section has a 3D shape. In embodiments, the cover may be made of a flexible material having a pre-set or shape memory to match the curvature of the top of the breast implant or breast itself. The physician may select a sizing and curvature of the cover to match the patient anatomy or target patient anatomy. Fabrication and use of shape memory materials including shaped full contour meshes are described in various publications including, e.g., US Patent Publication No. 20190247180, filed Jan. 30, 2019, entitled "FULL CONTOUR BREAST IMPLANT", incorporated herein by reference in its entirety for all purposes.

The wraps are preferably made from resorbable polymers, more preferably from resorbable fibers, and even more preferably from resorbable fibers that degrade in less than 5 years, more preferably in less than 2 years, and even more preferably in less than 1 year. The wraps may comprise fibers with fast and slow rates of degradation.

The wrap may have a two-dimensional shape that can be formed into a dome shape, round shape, spherical shape, three-dimensional shape, or anatomical shape.

Preferably, there is minimal or no wrinkling of the wrap when it is wrapped around the breast implant. In embodiments, the device is wrinkle or crease-free after being wrapped around the breast implant.

The volume enclosed by the wrap is preferably not more than 20% larger, more preferably not more than 10% larger, and even more preferably not more than 5% larger than the breast implant.

In other embodiments, the wraps have an elasticity that allows a tight fit to be formed between the wrap and the breast implant. Preferably, the volume enclosed by the wrap is no more than 20% larger than the volume of the breast implant, more preferably no more than 10% larger than the volume of the breast implant, and even more preferably no more than 5% larger than the volume of the breast implant. Preferably, the volume enclosed by the wrap is between 150-800 cc, and more preferably between 165-800 cc.

In another embodiment, the wrap is configured to form an unstretched volume slightly (e.g., 5-10%) less than the volume of the breast implant. When the breast implant is wrapped by the device, the device stretches to accommodate the entire contour of the breast implant. The fit is snug and substantially wrinkle-free.

The wrap preferably has a shape that allows it to at least partially cover the breast implant without any unnecessary protuberances that would interfere with implantation in the breast, or detract from the final appearance of the breast.

In an embodiment, the breast implant fixation wrap devices further comprise one or more connectors that can be used to secure the breast implant inside the wrap.

In embodiments, the breast implant fixation wrap devices further comprise one or more tabs. The one or more tabs may be used to anchor the wraps in place in the patient. For example, the tabs may be anchored by suturing or stapling. The tabs are placed so that they are located on the wrap on the opposite side to the breast implant, and more preferably, on the opposite side of the wrap to the breast implant and at one or more locations around the perimeter of the breast implant. In a preferred embodiment, the wraps comprise a tab that is located in a superior position when the wrap containing the breast implant is implanted in the breast. A wrap with a tab that can be fixated to the patient in a superior position, for example, fixated to the pectoralis major muscle, can be used to maintain the vertical positioning of the breast implant, minimize implant motion, and prevent inferolateral instability. Any number of tabs may be incorporated in to the wrap, including 1, 2, 3, 4, 5, 6, 7, 8, 9, 10, 11, and 12, but more preferably 4 straps can be incorporated spaced at 90 degrees from each other so that they are located around the perimeter of the breast implant. Most preferably, the tabs are positioned on the wrap so that they are located in superior, inferior, medial and lateral positions to the breast implant when the wrap containing the breast implant is placed in the breast of the patient.

In embodiments, the breast implant fixation wrap device is shaped and sized preferably to drape at least part, but more preferably all, of the breast implant. The size and shape of the wrap used in a procedure may be based upon the surgeon's and patient's choice of the breast implant size and shape, and the need to match those requirements closely to the wrap size and shape so that the breast implant is at least partially covered by the wrap, and secured in the wrap.

Preferably the wraps are porous, or become porous after implantation, and even more preferably the wraps are macro-porous or become macro-porous after implantation. In a preferred embodiment, the wraps comprise pores with average pore diameters of at least 100 μm, more preferably at least 250 μm, and even more preferably at least 500 μm. A particularly preferred pore diameter is 800 μm±300 μm. A particularly preferred pore size is 0.64 mm²±0.3 mm². The wraps may be prepared from porous materials, or they may be prepared from non-porous materials. In embodiments, wraps prepared from non-porous materials are then perforated.

In embodiments, the materials used to form the wraps have one or more of the following properties: (i) burst strength of 0.1 to 30 kgf/cm²; (ii) suture pullout strength of 1-7 kgf, and (iii) areal density of 40 to 190 g/m². In a particularly preferred embodiment, the wrap materials comprise poly-4-hydroxybutyrate or copolymer thereof or poly (butylene succinate) or copolymer thereof, even more preferably in the form of textiles or other porous constructs.

The breast implant fixation wrap devices may comprise the additives listed in Section II.B and the bioactive agents listed in Section II.C. The breast implant fixation wrap device may be coated with one or more of the following: a bioactive agent, antibiotic, antimicrobial, autologous fat, fat lipoaspirate, injectable fat, adipose cells, fibroblast cells, stem cells, collagen, and hyaluronic acid.

The manufactured wraps preferably have an endotoxin content of less than 20 endotoxin units making them suitable for implantation in a patient.

Examples of breast implants that may be contained in the wraps include silicone and saline breast implants, anatomic and round breast implants, and surface textured and non-textured breast implants. Non-limiting examples of breast implants include: (i) Mentor's MemoryShape® breast implants, MemoryGel® breast implants, and Spectrum® breast implants; (ii) Allergan's Natrelle® breast implants, including their gummy breast implants, Inspira® responsive, soft touch and cohesive breast implants, Natrelle® 410 anatomical implants, Natrelle® saline-filled breast implants, and Biocell™ breast implants; (iii) Sientra's Opus™ breast implants, including their smooth round, textured round and textured shaped, high strength cohesive breast implants, HSC and HSC+; (iv) Arion Laboratories' Monobloc® silicone and hydrogel-CMC breast implants; (v) Cereplas Cereform® breast implants; (vi) Establishment Labs' Motiva® breast implants, including their Ergonomix™ and Round breast implants; (vii) GC Aesthetics' Eurosilicone® and Nagor® breast implants, including Impleo™ CoGEL™, Round Collection by Eurosilicone®, The Matrix by Eurosilicone®, GFX™ by Nagor®, and RGI™ by Nagor® breast implants; (viii) Groupe Sebbin's inflatable, cohesive round, high cohesive round, short anatomical and tall anatomical breast implants; (ix) Guangzhou Wanhe Plastic Materials' Snow.Lambe, Crystal.Lambe, and Lambe breast implants; (x) Hans Biomed's BellaGel breast implants; (xi) Ideal Implant Incorporated's Ideal Implant® breast implants; (xii) Polytech Health and Aesthetics' Mesmo®, Polytxt®, Microthane®, SublimeLine® and Diagon\Gel® 4 Two breast implants; and (xiii) Silimed breast implants including conical, round and anatomical shapes. Additional examples of breast implants for use with embodiments of the subject invention are disclosed by Maxwell and Gabriel, The evolution of breast implants, Plast. Reconstr. Surg. 134:12S, 2014, and references therein, U.S. Pat. No. 10,052,192 to Schuessler, U.S. Pat. No. 6,074,421 to Murphy, U.S. Pat. No. 5,007,929 to Quaid, U.S. Pat. No. 8,211,173 to Keller, U.S. Pat. No. 4,960,425 to Yan, U.S. Pat. No. 4,380,569 to Shaw, U.S. Pat. No. 5,902,335 to Snyder, U.S. Pat. No. 3,293,663 to Cronin, U.S. Pat. No. 4,863,470 to Carter, U.S. Pat. No. 4,773,909 to Chaglassian, U.S. Pat. No. 6,074,421 to Murphy, U.S. Pat. No. 8,377,127 to Schuessler, and U.S. Pat. No. 8,043,373 to Schuessler.

A. Examples of Wrap Designs

In one preferred embodiment, the breast implant fixation wrap devices are designed to limit movement of breast implants using tabs in the cover sections and receiving slits for the tabs in the base sections. A diagram of a wrap (200) with tabs in the cover section and receiving slits for the tabs in the base section is shown in FIG. 2. The wrap may comprise a base section (210) suitable for wrapping the back of a breast implant (see FIGS. 1A, 1B, respectively for locations of back and front on a breast implant). The base section (210) is shown having a circular or ovular area. In embodiments, the base section shape can be roughly sized to match the shape of the back of the breast implant. In embodiments, the base section may have a shape that is not circular.

FIG. 2 also shows a cover section (220) suitable for wrapping the front of a breast implant. Unlike the base section (210), the cover section (220) shown in FIG. 2 shows a plurality of extension members 260, each of which terminates at a tab (230), described further herein. The extension members 260 are shown extending radially from the center of the cover (220). Adjacent extension members are defined or characterized by a gap, preferably a V-shaped cut out as shown in FIG. 2. However, the cutout or gaps may take other shapes such as, e.g., U-shape, bowl, or step. As described further herein, the presence of the extensions and cutouts facilitate a tight snug fit over the top of the breast implant and serve to eliminate creases and wrinkles.

A hinge section (250) joins the base section (210) and the cover section (220). The wrap (200) may fold along the hinge section (250) in order to allow the base section (210) and cover section (220) to at least partially cover a breast implant. After placement of the back of a breast implant on the base section (210) of the wrap (200), the cover section (220) may be wrapped over the front of the breast implant, and secured in place by inserting the tabs (230) on the cover section (220) into the slits (240) of the base section (210). The shape of the wrap and independent radiating extensions are adapted to follow the contours of the breast implant when the back of a breast implant is placed on the base section (210) of the wrap (200), and the cover section (220) is wrapped over the front of the breast implant. Without intending to be bound to theory, providing a cover having different geometry and characteristics than the base to which it is joined serves to reduce wrinkles and creases across the top of the breast implant after surgery.

Figure 6:
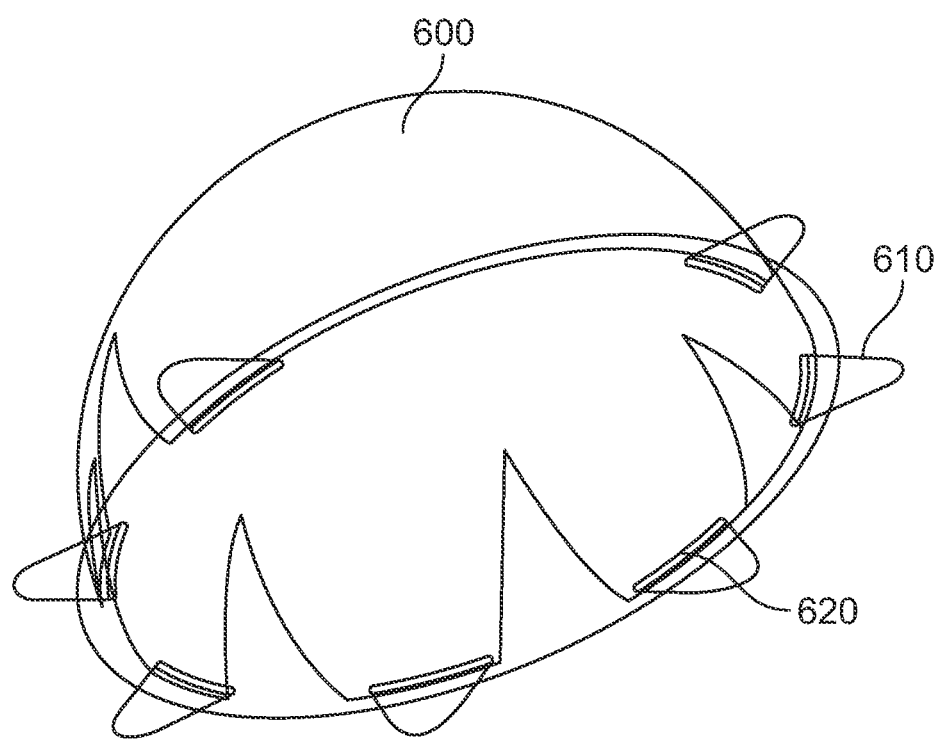
FIG. 6 shows a bottom side perspective view of a breast implant wrap (600) arranged in a 3D configuration in accordance with an embodiment of the invention where portions of the wrap are transparent or removed to more clearly illustrate features otherwise hidden from view.
Figure 7:
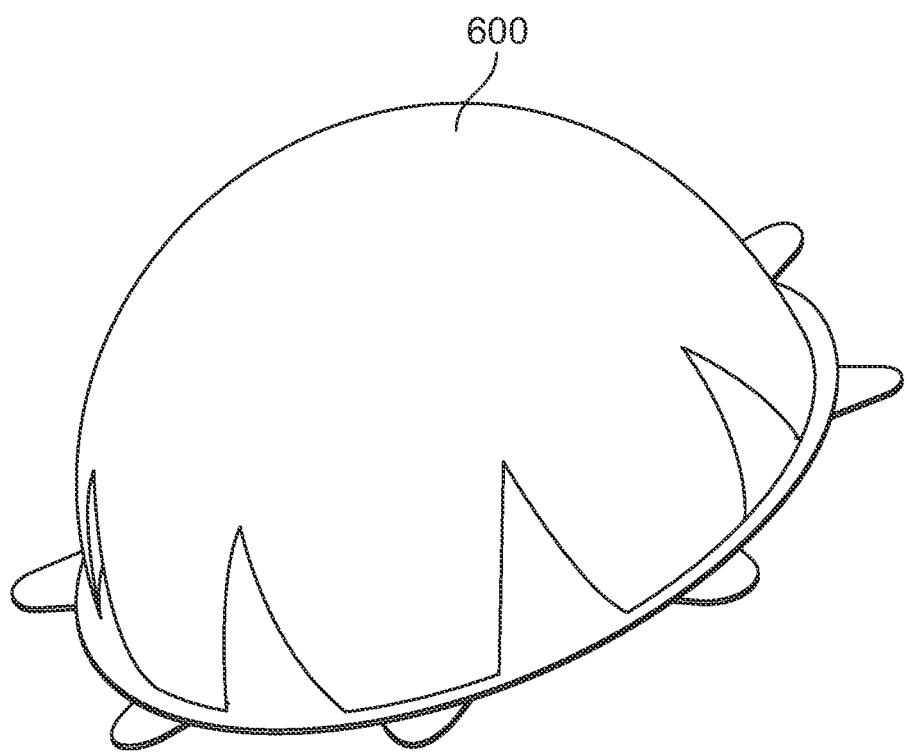
FIG. 7 shows a front side perspective view of the breast implant wrap (600) shown in FIG. 6.

FIGS. 6-7 show a bottom side perspective view and a top side perspective view, respectively, of a breast implant wrap (600) arranged in a 3D configuration in accordance with an embodiment of the invention. Tabs (610) of the cover section are shown extending from slits (620). In the embodiment shown in FIGS. 6-7, the tabs (610) serve to anchor the wrap in place in the patient as well as to connect the cover and bottom sections to one another.

In alternative embodiments, the tabs (230) may be attached to the base section (210), or to both the base and cover sections. Optionally, the tabs (230) may be fixated to the base section (210) after insertion into the slits (240). For example, by stitching, thermal bonding or use of an adhesive.

Optionally, although not shown, pleats or folds may be incorporated into one of the sections of the wrap in lieu of cutouts and are designed to minimize wrinkling of the wrap when it is used to cover the breast implant.

The tabs (230) may also be used for fixation of the wrap to the breast in the patient. Additionally, the wrap (200) may further comprise one or more additional tabs to allow fixation of the wrap in the breast. Preferably, the wrap (200) comprises a tab for fixation to the patient that can be located in a superior position when the wrap containing the breast implant is placed in the breast.

Figure 3:
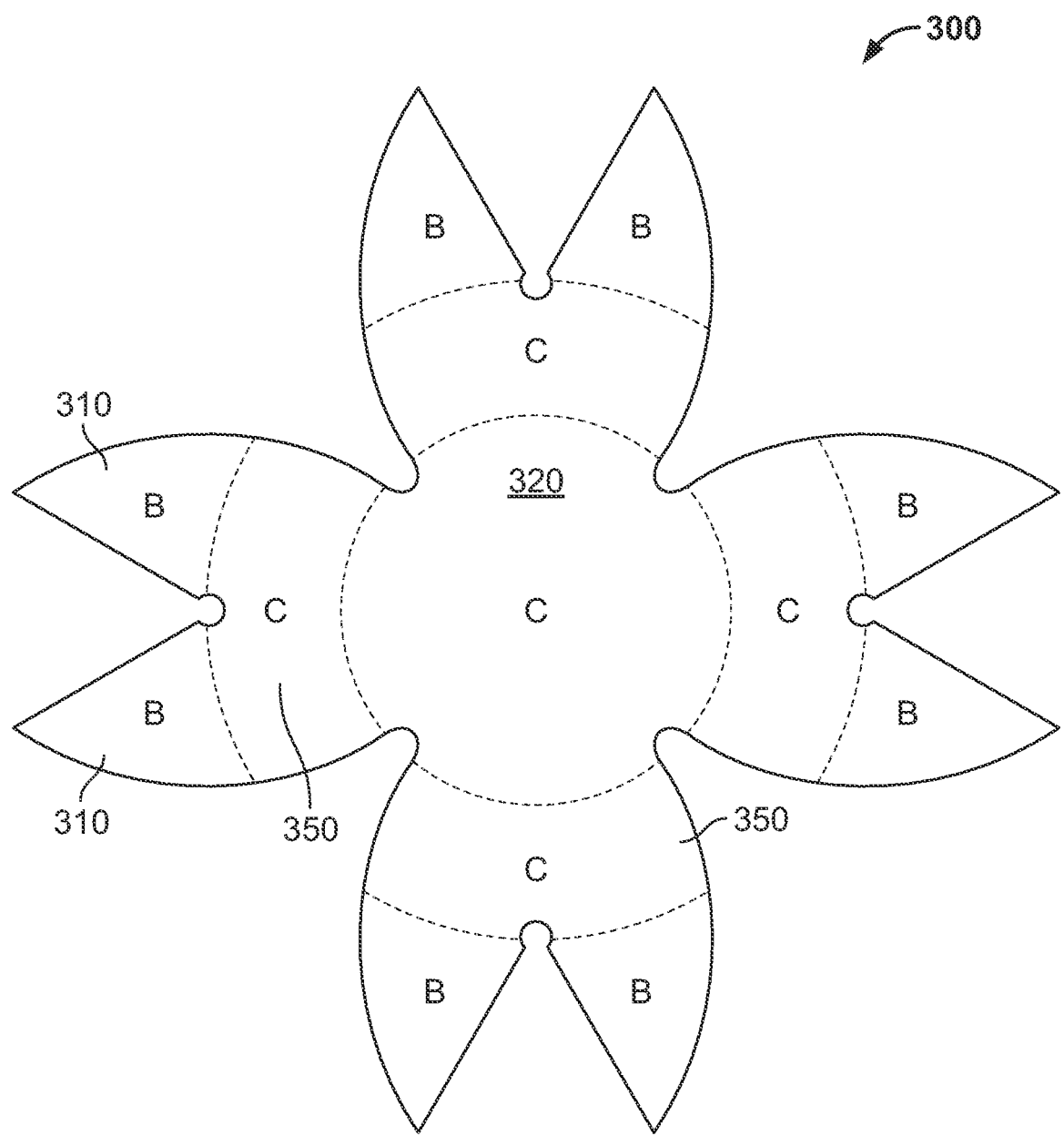
FIG. 3 shows a wrap (300) for a breast implant in accordance with an embodiment of the invention comprising a cover section (320) connected to eight base sections (310) via hinged sections (350). The base sections (310) can be folded around a breast implant and interlinked to secure the breast implant inside the wrap.

In another preferred embodiment, the wraps are designed to limit movement of breast implants using base sections that interlink with each other to secure breast implants within the wraps. A diagram of a wrap (300) with base sections that can interlink to wrap a breast implant is shown in FIG. 3. The wrap (300) comprises a cover section (320) for wrapping over the front of the breast implant, and eight base sections (310) connected to the cover section (320) by hinge regions (350). After placement of the front of a breast implant on the cover section (320) of the wrap, the eight base sections (310) connected to the hinge regions (350) may be folded over the back of the breast implant and interlinked in order to secure the breast implant inside the wrap (300). The wrap (300) is designed to minimize wrinkling of the wrap when the eight base sections (310) are interlinked to contain the breast implant. Optionally, the base sections (310) may be secured, for example, by stitching, thermal bonding, spot welding, or use of an adhesive.

The wrap (300) may further comprise one or more tabs (not shown) to allow fixation of the wrap in the breast. Preferably, the wrap (300) comprises a tab for fixation to the patient that can be located in a superior position when the wrap containing the breast implant is placed in the breast.

Figure 4:
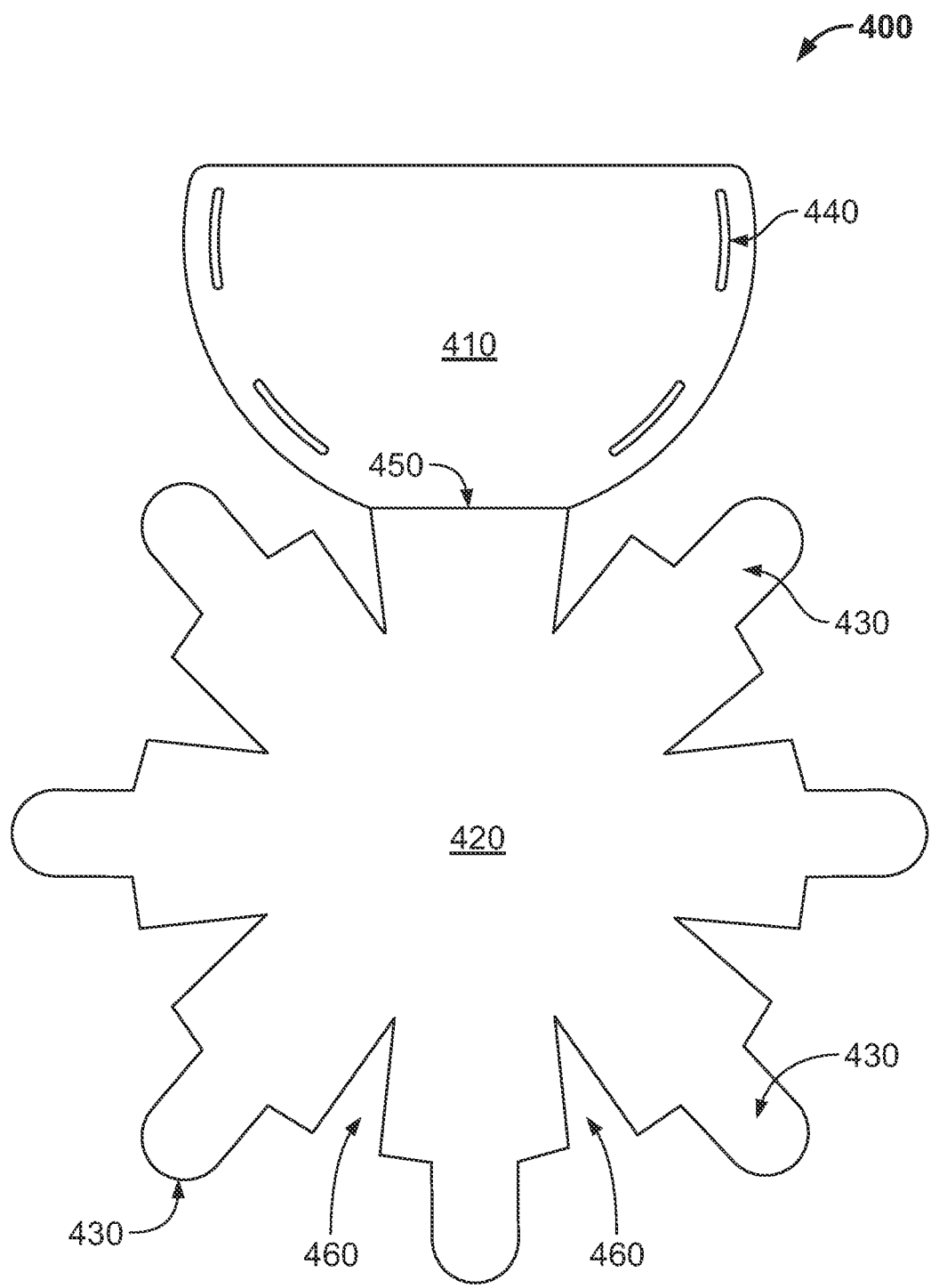
FIG. 4 shows a wrap (400) for a breast implant in accordance with an embodiment of the invention comprising a base section (410) with slits (440), a cover section (420) with tabs (430), and a hinge (450) connecting the base section (410) and cover section (420).

In another embodiment, the breast implant fixation wrap devices are designed so that the back of the breast implant is only partly covered. This design allows the surgeon to preassemble the wrap prior to inserting the breast implant. A diagram of a wrap (400) where the base of the breast implant is not fully covered during use of the device is shown in FIG. 4. The wrap comprises a base section (410) that approximates a half circle as opposed to the full circle (210) shown in FIG. 2. The half circle base section (410) is joined to a cover section (420) via a hinge region (450) as shown in FIG. 4. The cover section (420) comprises tabs (430) which can engage in the slits (440) of the base section (410). The wrap (400) may be assembled prior to surgery allowing a breast implant to be introduced after assembly of the device. Preferably, there is minimal wrinkling of the wrap (400) containing the breast implant. The gaps (460) in the wrap (400) are designed to minimize wrinkling of the wrap when it is used to cover the breast implant. Optionally, the tabs (430) may be fixated to the base section (410) after insertion into the slits (440). For example, by stitching, thermal bonding or use of an adhesive. The tabs (430) may also be used for fixation of the wrap to the patient. The wrap (400) may further comprise one or more additional tabs to allow fixation of the wrap in the breast. Preferably, the wrap (400) comprises a tab for fixation to the patient that can be located in a superior position when the wrap containing the breast implant is placed in the breast.

Figure 5:
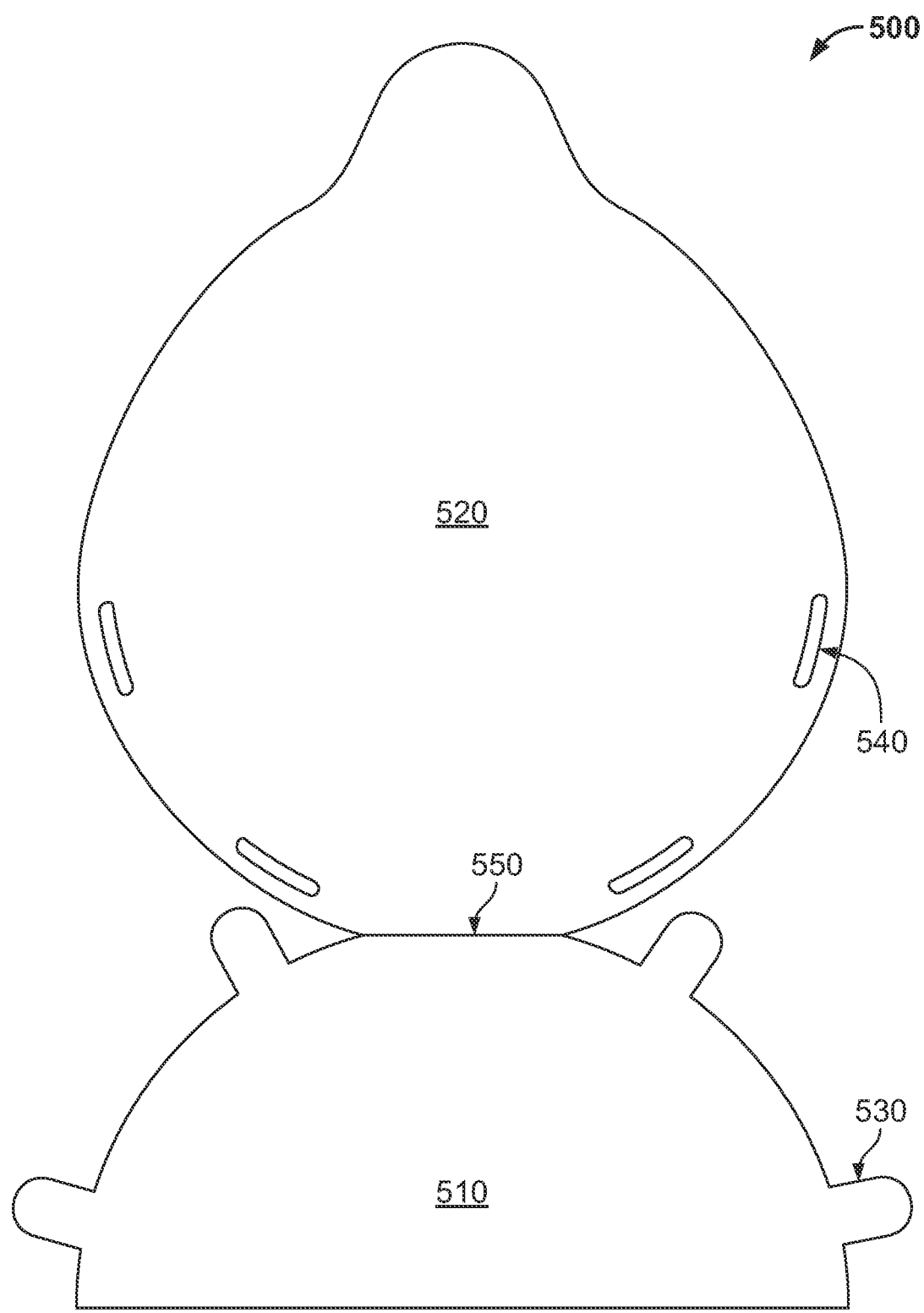
FIG. 5 shows a wrap (500) for a breast implant in accordance with an embodiment of the invention comprising a base section (510) with 4 tabs (530) and a cover section (520) with 4 slits (540), and a hinge region (550) connecting the base section (510) to the cover section (520).

In a further embodiment, the breast implant fixation wrap devices comprise stretchable fabrics, particularly in the cover sections. Preferably, the stretchable fabric stretches less than 50% under a bidirectional burst load. A diagram of a wrap design where the cover section comprises a stretchable fabric is shown in FIG. 5. In contrast to the wrap (400) shown in FIG. 4, where the cover section (420) has a design to minimize the formation of wrinkles, the cover section (520) of the wrap (500) in FIG. 5 does not contain gaps. Instead the cover section (520) of the wrap (500) comprises a stretchable fabric that does not form wrinkles when the cover section is wrapped around a breast implant. The wrap (500), like the wrap (400) may be assembled prior to surgery by placing the tabs (530) of the base section (510) in the slits (540) of the cover section, and then inserting a breast implant in the wrap. Alternatively, the back of a breast implant may be placed on the base section (510) of the wrap (500), and wrapped in the wrap by placing the cover section (520) over the front of the breast implant, and inserting the tabs (530) through the slits (540) to secure the breast implant in the wrap. In either case, the tabs (530) may be fixated to the cover section (520) after insertion in the slits (540) by, for example, stitching, thermal bonding, spot welding, or use of an adhesive. The tabs (530) may also be used for fixation of the wrap to the patient. The wrap (500) may further comprise one or more additional tabs to allow fixation of the wrap in the breast. Preferably, the wrap (500) comprises a tab for fixation to the patient that can be located in a superior position when the wrap containing the breast implant is placed in the breast. In embodiments, the wrap is formed such that the cover section (520) has a higher elasticity than the base section (510).

In another preferred embodiment, the wrap may comprise a base section and a separate cover section unconnected to the base section. The separate base and cover sections may be secured together to encapsulate the breast implant. The cover section preferably has a three-dimensional shape, and more preferably has a shape and size to cover the front of the breast implant. The cover section preferably is shaped to contour the front of the breast implant without wrinkling. The base section is preferably two-dimensional, but may have a three-dimensional shape wherein the perimeter of the base section has a concave shape. The concave shape may be designed to surround the perimeter of the breast implant and cover part of the top side (130) and bottom side (140) of the breast implant. The base section, cover section, or both sections may further comprise one or more tabs to secure the breast implant inside the wrap. The wrap may also be assembled around the breast implant by stitching, gluing or thermal bonding. The tabs may also be used for fixation of the wrap to the patient. The wrap may comprise one or more additional tabs for fixation of the device to the chest wall of the patient.

The wraps disclosed herein (e.g., without limitation, 200, 300, 400, 500) are designed so that the cover sections of the wraps preferably encompass most, and even more preferably all, of the projection of the breast implant from the chest of the patient. In an embodiment, the wraps are designed to accommodate projections of the breast implant from the chest wall ranging between 4 and 8.5 cm, and more preferably 4.2 and 7 cm.

The wraps disclosed herein (e.g., without limitation, 200, 300, 400, 500) preferably have base sections with widths ranging from 7.4 to 17.2 cm, and more preferably ranging from 9 to 16.5 cm.

The wraps disclosed herein may have base or cover sections comprising one or more circular-shaped portions or sectors.

The invention includes a wide range of mechanisms to attach the cover section of the wrap to the base section of the wrap. Exemplary mechanisms to connect the cover section to the base section and to secure the breast implants therein include, but are not limited to, sutures, tabs, slits, snap fasteners, ties, buckles, straps, and cords as well as thermal bonding, spot welding, or use of an adhesive.

B. Wraps with Different Thicknesses, Different Pore Sizes, and Different Elasticities In further embodiments, breast implant fixation wrap devices may be prepared from one or more materials with different pore sizes, one or more materials with different elasticities, or one or more materials with different thicknesses, or a combination thereof. In one embodiment, suitably shaped materials with different pore sizes, different thicknesses or both different pore sizes and different thicknesses may be joined together, for example, by sewing, gluing, or welding, in order to form a wrap for an implant. In another embodiment, a wrap may be cut from a sheet with different pore sizes, different thicknesses, or a combination thereof. The materials used to construct the wrap are preferably porous, and more preferably are textiles, including woven, non-woven, monofilament, multifilament, and knitted textiles. In a particularly preferred embodiment, the textiles are monofilament meshes, and even more preferably monofilament meshes with a Marlex knit pattern.

Preferably the cover section (e.g. 220, 320, 420) of the wrap (that is placed beneath the patient's skin) has a thickness of 0.5-10 mm, and the base section of the wrap (e.g. 210, 310, 410) (that is placed next to the chest wall) has a thickness of 0.2-0.6 mm. Wraps with thicker cover sections make it possible to avoid the formation of ripples and indentations on the patient's skin caused by ripples present on breast implants, and reduce or eliminate the palpability of the breast implant. Use of wraps with thicker cover sections is particularly important in patients where the skin is thin, or in patients where excessive amounts of tissue have been removed such as in radical mastectomy procedures.

In another embodiment, a wrap for fixation of a breast implant may be prepared with different pore sizes in different areas of the wrap. Preferably, the wrap is prepared with larger pores in the base section (e.g. 210, 310, 410) of the wrap (which contacts the chest wall after implantation), and smaller pores in the area of the cover section (e.g. 220, 320, 420) that covers the top side section of the breast implant (see FIG. 1B for location of "top side"). The latter area is located, after implantation, in the upper pole of the breast under the skin of the patient. The larger pores on the base section of the wrap improve the drapeability of the wrap. The smaller pores on the cover section of the wrap covering the top side of the breast implant increase the surface area available for coating with fat, and allow delivery of more fat to the upper pole of the breast. In a preferred embodiment, the average pore sizes in the different areas of the wraps are: 0.5-3 mm on the base section of the wrap, 0.1-1 mm on the cover section of the wrap in the area that covers the top side of the breast implant (see FIG. 1B for top side location), and 0.5-1 mm on the cover section of the wrap in the area that covers the bottom side of the breast implant (see FIG. 1A for bottom side location).

In an embodiment, the wrap has elasticity that makes it possible to easily wrap the breast implant with a tight fit. Preferably, the wrap is formed with the cover section (e.g. 220, 320, 420, 520) of the wrap (which is placed just under the patient's skin) having an elasticity of 15-75% or 30-65%, and the base section (e.g. 210, 310, 410, 510) of the wrap (which is placed on the chest wall of the patient) having an elasticity of 5-25% or 8-20%, wherein the elasticity is measured as the percent increase of the area when the area is subject to deformation in ASTM burst method D6797-02 using a round ball. In a particularly preferred embodiment, the wrap materials may be chosen so that the cover section of the wrap has an elasticity of 30-65%, and the base section of the wrap has an elasticity of 8-20%.

C. Fabrication of Wraps

In embodiments, wraps with tabs and slits (e.g. 200, 400, 500), or wraps with interlocking sections (e.g. 300), may be formed using fiber-based structures, including structures formed by melt-blowing, solution spinning, dry spinning, electrospinning, centrifugal spinning, melt spinning, knitting, weaving, braiding, entangling of fibers, 3D-printing, as well as embedded fibers in other structures such as foams, films, laminates, and fibers coated with films and foams. Fiber-based structures may comprise monofilament fibers, multifilament fibers, hollow fibers, and yarns. Fiber-based structures include non-woven structures, knitted structures, braided structures, textiles, fabrics, and woven structures. Preferred fiber-based structures are (i) knitted monofilament meshes, and even more preferably a knitted monofilament mesh comprising P4HB or copolymer thereof, or poly (butylene succinate) or copolymer thereof, and (ii) dry spun nonwovens, and even more preferably P4HB dry spun nonwovens or dry spun nonwovens of poly(butylene succinate) or copolymer thereof. In a particularly preferred embodiment, a wrap for a breast implant is formed from a knitted monofilament mesh comprising P4HB or copolymer thereof, or poly(butylene succinate) or copolymer thereof, or from a mesh prepared as described in Section II.G above. The monofilament preferably has an average fiber diameter from 0.04 mm to 0.35 mm, but more preferably 0.05 to 0.2 mm. The wraps shown in FIG. 2 and FIG. 3 may be prepared from meshes of knitted monofilament fibers, and are cut to form the shapes shown in FIG. 2 and FIG. 3. The knitted meshes may be cut, for example, with a sharp blade, scissors, or using a laser.

In other embodiments, the cover section of the wrap (e.g. 220, 320, 420, 520) may be formed from a non-fiber-based structure, such as a film, laminate, or foam, or structure comprising a combination of fibers, films or foams. The cover section of the wrap may also be formed from a non-porous structure, and later perforated.

A breast implant fixation wrap device can be prepared, for example, using the following method steps: (i) preparing a monofilament knitted mesh, (ii) preparing a template, for example, in the shapes shown in FIG. 2-5, (iii) placing the template on the knitted mesh, and (iv) cutting around the template to form the wrap. The mesh is ideally cut with a laser, but may also be cut with scissors, die set, or a sharp blade. Preferably, the knitted mesh used in this method is a warp knitted monofilament mesh, and even more preferably a warp knit monofilament mesh comprising P4HB or copolymer thereof, or comprising poly(butylene succinate) or copolymer thereof. In a further embodiment, tabs may be added to the wrap for fixation of the wrap to the patient. Or, alternatively, the template may be modified so that mesh tabs are formed when the wrap is cut from the mesh. Preferably, the mesh tabs are located around the perimeter of the base section of the wrap.

The breast implant fixation wrap devices may also be prepared from non-woven constructs. A wrap can be prepared, for example, using the following method steps: (i) preparing a non-woven construct, (ii) preparing a template, for example, in the shapes shown in FIG. 2-5, (iii) placing the template on the non-woven construct, and (iv) cutting around the template to form the wrap. A particularly preferred polymer for preparing a non-woven wrap is P4HB or copolymer thereof. Another particularly preferred polymer for preparing a non-woven wrap is poly(butylene succinate) or copolymer thereof. P4HB and poly(butylene succinate) or copolymers thereof may be dry spun to form non-wovens without any significant loss of weight average molecular weight. In a preferred embodiment, the P4HB and poly (butylene succinate) or copolymers thereof do not lose more than 10% of their weight average molecular weights during dry spinning of the non-woven.

In another embodiment, the wraps for breast implant fixation are formed by 3D-printing. Suitable methods for 3D-printing the wraps include fused filament fabrication, fused pellet deposition, melt extrusion deposition, selective laser melting, printing of slurries and solutions using a coagulation bath, and printing using a binding solution and granules of powder. Preferably, the wraps are 3D-printed using P4HB or poly(butylene succinate) or copolymer thereof.

In another embodiment, the wraps for breast implant fixation are formed by preparing a base section (e.g. 220, 320, 420, 520) of the wrap from a first mesh, and a cover section (e.g. 210, 310, 410, 510) of the wrap from a second mesh, and ultrasonically sealing or heat sealing the two meshes together at a hinge. In embodiments, the second mesh is able to stretch more than the first mesh. In embodiments, the second mesh has a higher elasticity than the first mesh. In embodiments, the first and second meshes are knit with fibers, and the average diameter of the fibers used to knit the first mesh is larger than the average diameter of the fibers used to knit the second mesh. In embodiments, the fibers used to knit the first mesh have an average diameter of 0.1 to 0.149 mm. In embodiments, the fibers used to knit the second mesh have an average diameter of 0.07 to 0.099 mm. In embodiments, the first mesh has a Marlex knit pattern. In embodiments, the second mesh has a diamond knit pattern. In embodiments, the base section (e.g. 210, 310, 410, 510) is formed with a Marlex mesh knit pattern made of fibers with an average diameter of 0.1 to 0.149 mm, and the cover section (e.g. 220, 320, 420, 520) is formed with a diamond knit pattern made of fibers with an average diameter of 0.07 to 0.099 mm.

IV. Methods of Implanting Wraps Containing Breast Implants to Limit Movement The wraps containing the breast implants may be implanted in the body. Preferably, the assembly of the wrap containing the breast implant is implanted in the breast. More preferably, the wrap is implanted in a breast where the patient is seeking reconstruction or augmentation of the breast.

The breast implants are preferably wrapped in the wraps, or inserted in the wraps, prior to implantation, however, in certain embodiments the wrap may also be implanted in the patient, and then the breast implant placed in the wrap.

In a preferred embodiment, a method comprises providing a wrap in an initial flat or planar configuration. The flat or planar configuration comprises a base portion and a cover portion joined to the base portion at a hinge or joint. A breast implant is placed on the base portion and the cover portion is folded over the breast implant.

Next, the cover is pulled tightly over the breast implant and secured to the base portion such that wrinkles on the cover are removed.

Optionally, one or more tabs on the cover may be pulled tighter to the base to remove any folds or wrinkles present in the cover. In a preferred embodiment, and with reference again to FIG. 2, tabs (230) may be inserted through the slits (240) and pulled to secure the breast implant and to remove any folds or wrinkles present in the cover. The use of tabs and slits serves to provide the physician an implant-based mechanism to adjust the fit of the cover on the implant, and to adjust (namely, decrease) the number of folds or wrinkles on the cover. The implant is designed to provide a smooth surface to cover the front of the breast implant so that skin indentations or ripples are minimized or eliminated on the surface of the patient's breast. The tabs (230) are inserted into the slits (240) and secured so that the cover section (220) is able to cover the front of the breast implant without forming wrinkles that would be visible on the surface of the breast. Optionally, the tabs may be fastened to secure the breast implant in the wrap, for example, by stitching, molding, welding or use of adhesive.

In another preferred embodiment, a method comprises providing a wrap with a cover section and a separate base section. A breast implant is placed on the base section, and a cover section is placed on the front of the breast implant, or vice versa.

Next, the cover section and the base section are secured together such that wrinkles on the cover section are removed.

Optionally, the cover section and the base section are secured together with one or more tabs present on one or more sections.

In a preferred embodiment, the wrap containing the breast implant is used in breast reconstruction, particularly following mastectomy, and breast augmentation, including augmentation mastopexy. The wrap containing the breast implant may be placed in a pocket formed in the breast solely from the patient's tissues, or in a pocket that is formed using an implant, for example, a pectoralis extender, such as an acellular dermal matrix (ADM), P4HB mesh, mesh of poly(butylene succinate) or copolymer thereof, or other material that can form a hammock or sling in the breast. If desired the pocket may be formed or enlarged using a tissue expander.

In an embodiment, a procedure for implanting the wrap containing the breast implant following mastectomy comprises forming a pocket in the breast of a patient suitable for receiving the wrap containing the breast implant, and implanting the wrap containing the breast implant. In a preferred procedure for implanting the wrap containing the breast implant in a patient after mastectomy, the method of implantation comprises: (i) implanting a tissue expander in the patient; (ii) implanting a pectoralis extender in the vicinity of the tissue expander; (iii) expanding the tissue expander; (iv) removing the tissue expander; and (v) implanting the wrap containing the breast implant in the pocket created in the breast of the patient. Preferably, the pectoralis extender is sutured to the detached pectoralis major muscle, which has been mobilized in preparation for placement of a tissue expander. The suture may be either permanent or absorbable, but is preferably absorbable. Once sutured to the pectoralis major muscle, the pectoralis extender can be used as a sling or hammock to cover the inferolateral portion of an inserted tissue expander. The tissue expander may be partially inflated or uninflated prior to implantation. In the latter case, the tissue expander may be partially inflated immediately after implantation.

In an embodiment, a procedure for implanting the wrap containing the breast implant in patients desiring breast augmentation comprises implanting the wrapped breast implant in the pre-pectoral position (subglandular position) to eliminate the need to detach the muscle from the chest wall, and to reduce pain associated with detachment of the muscle from the chest wall. However, in other embodiments, the wrap containing the breast implant may, if desired, be implanted in the sub-pectoral position or sub-muscular position.

Preferably, the wrap containing the breast implant may be fixated in place. In an embodiment, the wrap comprises one or more tabs, or similar extensions, that may be fastened to the patient's tissue. The tabs may be fastened to the patient's tissue using sutures, tacks, clips, staples, or similar fastening devices. In a particularly preferred implantation method, the wrap comprises a superior tab that is located in a superior position in the patient. The superior tab can be used to fixate the wrap to the pectoralis major muscle in order to maintain the vertical positioning of the breast implant, prevent inferolateral instability, and minimize implant motion. Alternatively, the wraps may be fixated in place by directly attaching the wrap to the chest wall of the patient, for example, using sutures, tacks, staples or other fastening devices and materials.

We claim:

1. A breast implant fixation device to secure a breast implant in a patient comprising:
    a base section, a cover section, and a hinge region connecting the base section to the cover section;
    wherein said implant fixation device comprises a substantially planar two dimensional first configuration; and
    a folded three dimensional second configuration comprising a shape and size to at least partially cover the breast implant when the cover section is wrapped around the front of the breast implant and secured to the base section; and
    wherein the base section and the cover section each have a plurality of pores, wherein the average diameter of the pores in the cover section is smaller than the average diameter of the pores in the base section, and wherein the cover section has a greater elasticity than the base section.

2. The device of claim 1, wherein the cover section has an elasticity of 15-75%.

3. The device of claim 1, wherein the base section has an elasticity of 5-25%.

4. The device of claim 1, further comprising one or more tabs for anchoring the device to the patient's chest wall to prevent movement of the breast implant.

5. The device of claim 1, wherein the thickness of the cover section is greater than the thickness of the base section.

6. The device of claim 1, wherein the base section is formed from a first mesh, and the cover section is formed from a second mesh, and wherein the elasticity of the second mesh is greater than the elasticity of the first mesh.

7. The device of claim 6, wherein the first and second meshes are formed from fibers and the average diameter of the fibers forming the first mesh is larger than the average diameter of the fibers forming the second mesh.

8. The device of claim 1, further comprising a plurality of tabs, and a plurality of slits, wherein each slit is adapted to receive one tab such that the cover can be tightened to eliminate wrinkles in the cover.

9. A breast implant wrap comprising:
    a thin sheet-like two dimensional first configuration, said first configuration further comprising a base section, a cover section, and a hinge region connecting the base section to the cover section; and
    a second three dimensional configuration comprising a shape and size to at least partially cover the breast implant when the cover section is folded around the front of the breast implant and secured to the base section, wherein the cover section has a greater elasticity than the base section.

10. The breast implant wrap of claim 9, wherein the cover section has a profile selected from the group consisting of: star, flower, and gear.

11. The breast implant wrap of claim 10, wherein the cover section has a center area and plurality of extension members (or fingers, petals or teeth) radially extending from the center area.

12. The breast implant wrap of claim 11, wherein the number of extension members ranges from 4 to 8.

13. The breast implant wrap of claim 9, wherein the base section has a profile selected from the group consisting of: circle, semi-circle, droplet, and ellipse.

14. A method for performing breast implant surgery comprising:
   providing a wrap, the wrap comprising a pocket-free, substantially planar first configuration;
   placing the breast implant on a base section of the wrap and folding a cover section over the front of the breast implant such that the wrap forms a 3D second configuration enclosing the breast implant, wherein the cover section has a greater elasticity than the base section;
   adjusting the tightness of the cover over the top of the breast implant to remove wrinkles and creases across the breast implant;
   securing the cover to the base while the cover is stretched; and
   locating the wrap containing the breast implant in the breast of a patient.

15. The method of claim 14, wherein the securing step is performed by interlocking a plurality of radially extending teeth with a plurality slits, each slit being adapted to receive an individual tooth.

16. A breast implant fixation device to secure a breast implant in a patient comprising:
   a base section, a cover section, and a hinge region connecting the base section to the cover section;
   wherein said implant fixation device comprises a substantially planar two dimensional first configuration; and
   a folded three dimensional second configuration comprising a shape and size to at least partially cover the breast implant when the cover section is wrapped around the front of the breast implant and secured to the base section; and
   wherein the cover section has a greater elasticity than the base section, and wherein the thickness of the cover section is greater than the thickness of the base section.

17. The device of claim 16, wherein the cover section has an elasticity of 15-75%.

18. The device of claim 16, wherein the base section has an elasticity of 5-25%.

19. The device of claim 16, further comprising one or more tabs for anchoring the device to the patient's chest wall to prevent movement of the breast implant.

20. The device of claim 16, wherein the base section is formed from a first mesh, and the cover section is formed from a second mesh, and wherein the elasticity of the second mesh is greater than the elasticity of the first mesh.

21. The device of claim 20, wherein the first and second meshes are formed from fibers and the average diameter of the fibers forming the first mesh is larger than the average diameter of the fibers forming the second mesh.

22. The device of claim 16, further comprising a plurality of tabs, and a plurality of slits, wherein each slit is adapted to receive one tab such that the cover can be tightened to eliminate wrinkles in the cover.

23. A breast implant fixation device to secure a breast implant in a patient comprising:
   a base section, a cover section, and a hinge region connecting the base section to the cover section;
   wherein said implant fixation device comprises a substantially planar two dimensional first configuration; and
   a folded three dimensional second configuration comprising a shape and size to at least partially cover the breast implant when the cover section is wrapped around the front of the breast implant and secured to the base section; and
   wherein the base section is formed from a first mesh, and the cover section is formed from a second mesh, and wherein the elasticity of the second mesh is greater than the elasticity of the first mesh.

24. The device of claim 23, wherein the cover section has an elasticity of 15-75%.

25. The device of claim 23, wherein the base section has an elasticity of 5-25%.

26. The device of claim 23, further comprising one or more tabs for anchoring the device to the patient's chest wall to prevent movement of the breast implant.

27. The device of claim 23, wherein the first and second meshes are formed from fibers and the average diameter of the fibers forming the first mesh is larger than the average diameter of the fibers forming the second mesh.

28. The device of claim 23, further comprising a plurality of tabs, and a plurality of slits, wherein each slit is adapted to receive one tab such that the cover can be tightened to eliminate wrinkles in the cover.

* * * * *